(12) United States Patent
Choy et al.

(10) Patent No.: US 9,339,018 B2
(45) Date of Patent: May 17, 2016

(54) SELECTIVE INFARCTED-TISSUE-TARGETING BACTERIA AND USE THEREOF

(75) Inventors: Hyon El Choy, Seoul (KR); Jung-Joon Min, Gwaangju (KR); Hyung Seok Kim, Gwangju (KR); Yeongjin Hong, Gwangju (KR)

(73) Assignee: INDUSTRY FOUNDATION OF CHONNAM NATIONAL UNIVERISTY, Gwangju (KR)

( * ) Notice: Subject to any disclaimer, the term of this patent is extended or adjusted under 35 U.S.C. 154(b) by 417 days.

(21) Appl. No.: 13/322,637

(22) PCT Filed: May 27, 2010

(86) PCT No.: PCT/KR2010/003385
§ 371 (c)(1),
(2), (4) Date: Feb. 8, 2012

(87) PCT Pub. No.: WO2010/137900
PCT Pub. Date: Dec. 2, 2010

(65) Prior Publication Data
US 2012/0128594 A1    May 24, 2012

(30) Foreign Application Priority Data
May 27, 2009    (KR) .......................... 10-2009-0046459

(51) Int. Cl.
| A61K 48/00 | (2006.01) |
| A61K 35/74 | (2015.01) |
| A61K 49/00 | (2006.01) |
| A01K 67/027 | (2006.01) |
| C07K 14/255 | (2006.01) |
| A61K 35/00 | (2006.01) |

(52) U.S. Cl.
CPC ........... *A01K 67/027* (2013.01); *A61K 48/0033* (2013.01); *C07K 14/255* (2013.01); *A01K 2207/12* (2013.01); *A01K 2227/105* (2013.01); *A01K 2267/0375* (2013.01); *A61K 2035/11* (2013.01); *C12N 2830/001* (2013.01)

(58) Field of Classification Search
None
See application file for complete search history.

(56) References Cited

U.S. PATENT DOCUMENTS

2004/0248796 A1* 12/2004 Alitalo et al. ................... 514/12
2006/0251663 A1* 11/2006 Mariscal-Gonzalez et al. .......................... 424/159.1

OTHER PUBLICATIONS

Lee et al. J. Gene Med. 6: 1382-1393, 2004.*
Feng et al. Ali Zheng. 24: 548-553, 2005, abstract.*
Na et al. Vaccine 24: 2027-2034, 2006.*
Bougioukas et al. Cardiovascular Pathology 16: 63-68, 2007.*
Shinohara et al. Hokkaido Igaku Zasshi 69: 978-993, 1994, abstract.*
Yockman et al. Gene Therapy 16: 127-135, published online Sep. 11, 2008.*
Ruixing et al. Growth Factors 24: 209-217, 2006, abstract.*
Forbes et al., "Sparse Initial Entrapment of Systemically Injected *Salmonella typhimurium* Leads to Heterogeneous Accumulation within Tumors", Cancer Res., 63(17): 5188-5193, 2003.
Rudd et al., "Mutations in the spoT Gene of *Salmonella typhimurium*: Effects on his Operon Expression", J. Bacteriol., 163(2): 534-542, 1985.
Jiang et al., "Using Attenuated *Salmonella typhi* as Tumor Targeting Vector for MDR1 siRNA Delivery", Cancer Biol. Ther, 6(4): el-e6, 2007.
Liu et al., "Anticancer efficacy of systemically delivered anaerobic bacteria as gene therapy vectors targeting tumor hypoxia/necrosis", Gene Ther., 9: 291-296, 2002.

\* cited by examiner

*Primary Examiner* — S. Devi
(74) *Attorney, Agent, or Firm* — Ann Wieczorek; Mayer & Williams PC

(57) ABSTRACT

The present invention relates to bacteria which specifically target infarcted tissue and use thereof. The present invention provides a selective infarcted tissue-targeting bacterium for the first time, and can be used in selectively delivering drugs to the infarcted tissue or in selectively imaging the infarcted tissue. The infarcted tissue-targeting bacterium of the present invention can finish treatments by using antibiotics, and therefore, have remarkable advantages as compared to gene therapy using recombinant viruses. The infarcted tissue-targeting bacterium of the present invention have a significantly high affinity and specificity to infarcted myocardium or infarcted brain, thereby significantly reducing undesired transfections in the organs or tissues other than the heart. The gene expression by the infarcted tissue-targeting bacterium of the present invention in infarcted myocardium or infarcted brain is remotely controllable.

4 Claims, 24 Drawing Sheets
(3 of 24 Drawing Sheet(s) Filed in Color)

SEQUENCE LISTING

```
<160> NUMBER OF SEQ ID NOS: 9

<210> SEQ ID NO 1
<211> LENGTH: 577
<212> TYPE: DNA
<213> ORGANISM: Homo sapiens
```

<400> SEQUENCE: 1

```
atgaactttc tgctgtcttg ggtgcattgg agccttgcct tgctgctcta cctccaccat    60
gccaagtggt cccaggctgc acccatggca gaaggaggag ggcagaatca tcacgaagtg   120
gtgaagttca tggatgtcta tcagcgcagc tactgccatc caatcgagac cctggtggac   180
atcttccagg agtaccctga tgagatcgag tacatcttca agccatcctg tgtgcccctg   240
atgcgatgcg ggggctgctg caatgacgag ggcctggagt gtgtgcccac tgaggagtcc   300
aacatcacca tgcagattat gcggatcaaa cctcaccaag ccagcacat aggagagatg    360
agcttcctac agcacaacaa atgtgaatgc agaccaaaga agatagagc aagcaagaa     420
aatccctgtg gccttgctc agagcggaga aagcatttgt ttgtacaaga tccgcagacg    480
tgtaaatgtt cctgcaaaaa cacagactcg cgttgcaagg cgaggcagct tgagttaaac   540
gaacgtactt gcagatgtga caagccgagg cggtgag                            577
```

<210> SEQ ID NO 2
<211> LENGTH: 191
<212> TYPE: PRT
<213> ORGANISM: Homo sapiens

<400> SEQUENCE: 2

```
Met Asn Phe Leu Leu Ser Trp Val His Trp Ser Leu Ala Leu Leu Leu
  1               5                  10                  15
Tyr Leu His His Ala Lys Trp Ser Gln Ala Ala Pro Met Ala Glu Gly
                 20                  25                  30
Gly Gly Gln Asn His His Glu Val Val Lys Phe Met Asp Val Tyr Gln
             35                  40                  45
Arg Ser Tyr Cys His Pro Ile Glu Thr Leu Val Asp Ile Phe Gln Glu
         50                  55                  60
Tyr Pro Asp Glu Ile Glu Tyr Ile Phe Lys Pro Ser Cys Val Pro Leu
 65                  70                  75                  80
Met Arg Cys Gly Gly Cys Cys Asn Asp Glu Gly Leu Glu Cys Val Pro
                 85                  90                  95
Thr Glu Glu Ser Asn Ile Thr Met Gln Ile Met Arg Ile Lys Pro His
                100                 105                 110
Gln Gly Gln His Ile Gly Glu Met Ser Phe Leu Gln His Asn Lys Cys
            115                 120                 125
Glu Cys Arg Pro Lys Lys Asp Arg Ala Arg Gln Glu Asn Pro Cys Gly
        130                 135                 140
Pro Cys Ser Glu Arg Arg Lys His Leu Phe Val Gln Asp Pro Gln Thr
145                 150                 155                 160
Cys Lys Cys Ser Cys Lys Asn Thr Asp Ser Arg Cys Lys Ala Arg Gln
                165                 170                 175
Leu Glu Leu Asn Glu Arg Thr Cys Arg Cys Asp Lys Pro Arg Arg
            180                 185                 190
```

<210> SEQ ID NO 3
<211> LENGTH: 468
<212> TYPE: DNA
<213> ORGANISM: Homo sapiens

<400> SEQUENCE: 3

```
atggctgaag ggaaatcac caccttcaca gccctgaccg agaagtttaa tctgcctcca    60
gggaattaca agaagcccaa actcctctac tgtagcaacg ggggccactt cctgaggatc   120
cttccggatg gcacagtgga tgggacaagg gacaggagcg accagcacat tcagctgcag   180
```

```
ctcagtgcgg aaagcgtggg ggaggtgtat ataaagagta ccgagactgg ccagtacttg      240
gccatggaca ccgacgggct tttatacggc tcacagacac caaatgagga atgtttgttc      300
ctggaaaggc tggaggagaa ccattacaac acctatatat ccaagaagca tgcagagaag      360
aattggtttg ttggcctcaa gaagaatggg agctgcaaac gcggtcctcg gactcactat      420
ggccagaaag caatcttgtt tctccccctg ccagtctctt ctgattaa                   468
```

```
<210> SEQ ID NO 4
<211> LENGTH: 155
<212> TYPE: PRT
<213> ORGANISM: Homo sapiens

<400> SEQUENCE: 4

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

```
<210> SEQ ID NO 5
<211> LENGTH: 6
<212> TYPE: PRT
<213> ORGANISM: Artificial Sequence
<220> FEATURE:
<223> OTHER INFORMATION: laminin alpha 1-derived peptide

<400> SEQUENCE: 5

Ser Ile Lys Val Ala Val
 1               5
```

```
<210> SEQ ID NO 6
<211> LENGTH: 43
<212> TYPE: DNA
<213> ORGANISM: Artificial Sequence
<220> FEATURE:
<223> OTHER INFORMATION: hVEGF165 forward primer

<400> SEQUENCE: 6
catggcccaa ccggccatgg ccatgaactt tctgctgtct tgg                        43
```

```
<210> SEQ ID NO 7
<211> LENGTH: 25
<212> TYPE: DNA
<213> ORGANISM: Artificial Sequence
```

```
<220> FEATURE:
<223> OTHER INFORMATION: hVEGF165 reverse primer

<400> SEQUENCE: 7
agtgtcgact caccgcctcg gcttg                                          25

<210> SEQ ID NO 8
<211> LENGTH: 40
<212> TYPE: DNA
<213> ORGANISM: Artificial Sequence
<220> FEATURE:
<223> OTHER INFORMATION: hFGF1a forward primer

<400> SEQUENCE: 8
catggcccaa ccggccatgg ccatggctga aggggaaatc                          40

<210> SEQ ID NO 9
<211> LENGTH: 32
<212> TYPE: DNA
<213> ORGANISM: Artificial Sequence
<220> FEATURE:
<223> OTHER INFORMATION: hFGF1a reverse primer

<400> SEQUENCE: 9
agtgtcgact taatcagaag agactggcag gg                                  32
```

SELECTIVE INFARCTED-TISSUE-TARGETING BACTERIA AND USE THEREOF

TECHNICAL FIELD

The present invention is drawn to bacteria capable of targeting infarcted tissues and use thereof.

BACKGROUND

Some bacteria such as *Escherichia coli*[1-3], *Salmonella*[3-9], *Clostridum*[10-12] and *Bifidobacterium*[13,14] are known to colonize and grow in tumor. In addition, recent studies showed that bacteria target primary tumors and metastasized tumors[1-3]. This feature has been used for vectors for tumor specific gene deliveryl[15-18]. Bacteria transformed with bioluminescent[1-3] or fluorescent[4,5] reporter gene were produced in order to monitor bacteria in vivo and the bacteria were used for tracking the movement thereof in model animals. As a result, the fates of the luminescent or fluorescent bacteria can be tracked noninvasively and reproducibly.

Abnormal supply of blood vessels found in tumors is a major factor for bacterial targeting[18]. Newly formed blood vessels in growing tumors are disorganized seriously and have imperfect endothelial lining and blind roof and result in insufficient blood stream and scant supplies of nutrients and oxygen[19,20]. It is presumed that poor nutrient delivery and oxygen deficiency induce hypoxic/anaerobic condition in tumor tissues and promote growth of obligatory and facultative anaerobic bacteria. According to previous report of the present inventors, facultative anaerobic bacteria including *E. coli* expressing lux operon (pLux) and *Salmonella typhimurium* having deficiency of ppGpp producing (ΔppGpp strain) target various solid tumor and the bacteria located preferentially in boundary region between peripheral proliferating region and central necrotic region[2]. The lux operon of *Photobacterium leognathi* encodes all proteins required to produce bioluminescence.

This document refers to several papers and patent documents and citations thereof are indicated throughout the document. The disclosures of the cited papers and patent documents are herein entirely incorporated by reference and thus the level of technical field to which the present invention belong and contents of the present invention are explained more definitely.

SUMMARY OF INVENTION

The present inventors made an effort to discover bacteria capable targeting infarcted tissues, especially infarcted myocardium and infarcted brain. As a result, the present inventors completed the present invention founding that obligatory or facultative anaerobic bacteria specifically target infarcted tissues and grow therein and confirming that it is possible to deliver pharmaceutical agents for treating or imaging myocardial infarction or brain infarction selectively to the infarcted tissues using the bacteria.

Therefore, the purpose of the present invention is to provide a drug delivery system for targeting infarcted tissues.

Another purpose of the present invention is to provide a method of delivering pharmaceutical agent to infarcted tissues.

Another purpose of the present invention is to provide a pharmaceutical composition for treating infarcted tissues.

Another purpose of the present invention is to provide a pharmaceutical composition for imaging infarcted tissues.

Another purpose of the present invention is to provide a method of treating infarcted tissues.

Another purpose of the present invention is to provide a method of imaging infarcted tissues.

Another purpose of the present invention is to provide a pharmaceutical composition for inducing angiogenesis.

Another purpose of the present invention is to provide a method of inducing angiogenesis.

Another purpose of the present invention is to provide a drug delivery system for penetrating blood-brain barrier (BBB).

Another purpose of the present invention is to provide a method of delivering a pharmaceutical agent penetrating blood-brain barrier (BBB).

The other purposes and advantages of the present invention would be understood more definitely by following detailed description of invention, claims and drawings.

DETAILED DESCRIPTION OF INVENTION

According to an aspect of the present invention, a drug delivery system for delivering a pharmaceutical agent for the treatment of infarction to an infarcted tissue comprising an obligatory anaerobic bacterium or a facultative anaerobic bacterium is provided.

According to another aspect of the present invention, a method of delivering a pharmaceutical agent for the treatment of infarction to an infarcted tissue comprising administrating the drug delivery system and the pharmaceutical agent to a subject is provided.

The present inventors made an effort to discover bacteria targeting infarcted tissues, especially infarcted myocardium and infarcted brain. As a result, the present inventors completed the present invention founding that obligatory or facultative anaerobic bacteria preferentially target infarcted tissues and grow preferentially in the tissues and confirming that it is possible to deliver pharmaceutical agents for treating or imaging myocardial infarction or brain infarction selectively to the infarcted tissues using the bacteria.

The "drug delivery system for delivering a pharmaceutical agent for the treatment of infarction to an infracted tissue" referred herein may be alternatively represented as "an infarcted tissue-targeting bacterium".

In the present invention, the infarcted tissue-targeting bacterium may be an obligatory anaerobic bacterium or a facultative anaerobic bacterium. In a preferred embodiment, the infarcted tissue-targeting bacterium may be *Salmonella*, *Clostridium*, *Bifidobacterium*, *E. coli*, *Yersinia enterocohtica*, *Listeria monocytogenies*, *Mycoplasma hominis* or *Streptococcus*. In a more preferred embodiment, the infarcted tissue-targeting bacterium may be *Salmonella*, and more preferred *Salmonella* may be *Salmonella typhimurium*, *Salmonella choleraesuis* or *Salmonella enteriditis*, and the most preferred may *Salmonella typhimurium*.

According to a preferred embodiment, the infarcted tissue-targeting bacterium may be a mutant defective in ppGpp synthesis.

A major protein for producing ppGpp is ppGpp synthetase and genes encoding the same include relA gene and spoT gene. According to a preferred embodiment, the mutant defective in ppGpp synthesis may comprise inactivated relA or spoT gene encoding ppGpp synthetase for synthesizing ppGpp. More preferred embodiment, the mutant defective in ppGpp synthesis may comprise inactivated relA and spoT gene.

The term used herein to refer to relA gene or spoT gene, "inactivation" means any genetic modifications of a gene resulting in the impairment of transcription or translation of the gene or activity of the gene product. These genetic modifications may include the inactivation of promoter of the gene as well as the inactivation of coding sequence (CDS). It is possible to inactivate a targeted gene in a bacterial genome by substitution, insertion, deletion or combination of thereof in all or partial regions of the gene. For example, the deletion of a gene and the insertion of heterologous sequence into the gene may result in truncation, nonsense mutation, frameshift mutation and missense mutation of the gene, etc. These gene-specific inactivations may be performed by methods established in the art. In the meantime, the deletion of a gene may be performed by various mutagenesis methods known in the art. For instance, a deletion of re/A gene or spoT gene may be performed by PCR mutagenesis method or cassette mutagenesis method (Sambrook, J. et al, Molecular Cloning. A Laboratory Manual, $3^{rd}$ ed. Cold Spring Harbor Press (2001)).

Defectiveness in ppGpp synthesis contributes to targeting activity of bacteria to infarcted tissues.

In a preferred embodiment, the infarcted tissue-targeting bacterium may be an attenuated bacterium. The term used herein, "attenuated" means to modify a microbe as less pathogenic. Administrating the attenuated microbes to patients is performed in order to reduce toxicity and other side effects.

The attenuated bacterium may be produced by various methods known in the art. For example, the attenuation may performed by deletion or disruption of virulence factors essential for the survival of bacteria in host cells. The deletion and disruption may be performed by various methods known in the art, such as homologous recombination, chemical mutagenesis, UV-induced mutagenesis or transposon-induced mutagenesis.

Examples of virulence factors of *Salmonella* capable of attenuating if being deleted are as follows:

5'-adenosine monophosphate (Biochenko et al, 1987, *Bull. Eksp. Biol. Med.*, 103: 190-2), cytolysin (Libby et al, 1994, *Proc. Natl. Acad. Sci. USA*, 91: 489-493), defensin-resistant loci (Fields et al, 1989, *Science*, 243: 1059-62), DNAK (Buchmeier et al, 1990, *Science*, 248: 730-732), fimbriae (Ernst et al, 1990, *Infect. Immun.* 58: 2014-2016), GroEL (Buchmeier et al, 1990, *Science*, 248: 730-732), Inv loci (Ginocchio et al, 1992, *Proc. Natl. Acad. Sci. USA*, 89: 5976-5980), lipoprotein (Stone et al, 1992, *J. Bacteriol.*, 174: 3945-3952), LPS (Gianella et al, 1973, *J. Infect. Dis.*, 128: 69-75), PhoP and PhoQ (Miller et al, 1989, *Proc. Natl. Acad. Sci. USA*, 86: 5054-5058), Pho activator (Abshiro et al, 1993, *J. Bacteriol.*, 175: 3734-3743), PhoP and PhoQ regulator (Behlau et al., 1993, *J. Bacteriol*, 175: 4475-4484), porin (Tufano et al., 1988, *Eur. J. Epiderniol*, 4: 110-114), toxic factor (Loos et at, 1994, *Immun. Infekt*, 22:14-19; Sansonetti, 1992, *Rev. Prat.*, 42: 2263-2267).

Attenuated bacteria are described detailed in WO96/40238, thus the patent document is herein entirely incorporated by reference.

In the meantime, the attenuation of a bacterium may be accomplished by modifying bacterial component resulting in toxicity of the bacterium. For instance, LPS (lipopolysaccharide) and endotoxin are major pathogens of bacterial septicemia and attenuated bacteria may be produced by removing lipid A from LPS.

In a preferred embodiment, the infarcted tissue of the present invention may be an infarcted myocardium, an infarcted brain, a pulmonary embolism tissue or an infarcted spleen. In the most preferred embodiment, the infarcted tissue may be an infarcted myocardium. In the meantime, the infarction is mainly classified to white infarction and red infarction and the infarcted tissue-targeting bacterium is suitable for targeting the white infarction.

In a preferred embodiment, the pharmaceutical agent delivered by the infarcted tissue-targeting bacterium of the present invention may be a chemical compound, a peptide, a polypeptide, a nucleic acid, a carbohydrate or a lipid, but not limited thereto.

The infarcted tissue-targeting bacterium of the present invention selectively targets infarcted tissues and selectively grows therein. Therefore, it is possible to deliver pharmaceutical agents useful for treating infarction, diseases resulted from the infarction or disease inducing the infarction or imaging the infarction to the infarcted tissues, using the infarcted tissue-targeting bacterium of the present invention. The disease may be cardial infarction, brain infarction, heart failure, lung failure, stroke, cardiovascular diseases, cardiac insufficiency, coronary arteriosclerosis, peripheral arterial diseases and arteriosclerosis, and so on, but not limited thereto.

In a preferred embodiment, the pharmaceutical agent delivered by the infarcted tissue-targeting bacterium may be chemotherapeutic agents, and the bacterium may be genetically modified to produce the chemotherapeutic agents. It is preferred that the bacterium is modified to produce the chemotherapeutic agents metabolically rather than contains the chemotherapeutic agent internally.

The phrase used herein, "the infarcted tissue-targeting bacterium delivers a pharmaceutical agent" means that the infarcted tissue-targeting bacterium may have genes for producing the pharmaceutical agent, as well as the bacterium may contain the pharmaceutical agent internally.

Exemplifying pharmaceutical agents for treating myocardial infarction are as follows:

(a) Vasodilators
(i) nitrodilators (e.g.: isosorbide dinitrate, isosorbide mononitrate, nitroglycerin, erythrityl tetranitrate, pentaerythritol tetranitrate and sodium nitroprusside)
(ii) angiotensin converting enzyme inhibitors (e.g.: benazepril, captopril, enalapril, fosinopril, lisinopril, moexipril, quinapril and ramipril)
(iii) angiotensin receptor blockers (e.g.: candersartan, eprosartan, irbesartan, losartan, olmesartan, telmisartan and valsartan)
(b) Cardiac Depressants
(i) beta blockers (e.g.: carteolol, carvedilol, labetalol, nadolol, penbutolol, pindolol, propranolol, sotalol, timolol, acebutolol, atenolol, betaxolol, bisoprolol, esmolol and metoprolol)
(c) Analgesics
(i) morphine.

In addition, the infarcted tissue-targeting bacterium of the present invention may deliver peptides, polypeptides or nucleic acids to infarcted tissues.

The phrase used herein, "the infarcted tissue-targeting bacterium delivers peptides, polypeptides or nucleic acids" means that the infarcted tissue-targeting bacterium may have genes for producing the peptides, polypeptides or nucleic acids, as well as the bacterium may contain the peptides, polypeptides or nucleic acids internally.

For example, the infarcted tissue-targeting bacterium of the present invention may contain a heterologous gene encoding a protein useful for treating infarction or siRNA or shRNA. In this case, the infarcted tissue-targeting bacterium plays a role as a gene therapeutic agent.

In a preferred embodiment of the present invention, the pharmaceutical agent is a therapeutic protein selected from a group consisting of VEGF (vascular endothelial growth factor), PIGF (placenta growth factor), myogenic protein, angiogenic cytokine (e.g., interleukin-8, TNF-α), SIKVAV (SEQ ID NO: 5) peptide and neuropeptide Y or a polynucleotide encoding the therapeutic protein. In addition, siRNAs or shRNAs inhibiting genes related to the degeneration of hypoxia inducible factor-1 (e.g., prolyl hydroxylase-2, PH2) may be included in the pharmaceutical agent. The sequence of the delivered heterologous nucleic acid molecule may be obtained from GenBank and EMBL.

In a preferred embodiment, the delivered heterologous nucleic acid molecule may be operably linked to a promoter capable of operating in the infarcted tissue-targeting bacterium. The term used herein, "operably linked to" means a functional linkage between nucleic acid expression regulatory sequences (e.g.: promoter, signal sequence or array of transcription factor binding sites) and other nucleotide sequences and thus the nucleic acid expression regulatory sequences may regulate the transcription and/or the translation of the other nucleotide sequences. In a preferred embodiment of the present invention, the delivered heterologous nucleic acid molecule may be delivered by being constructed as a vector system. The vector system may be constructed by various methods known in the art and particular methods are disclosed in Sambrook et al, Molecular Cloning, A Laboratory Manual, Cold Spring Harbor Laboratory Press (2001). The above document is herein entirely incorporated by reference. For example, it is usual that the vector system contains a promoter capable of transcripting the delivered heterologous nucleic acid molecule (e.g., tac promoter, lac promoter, lacUV5 promoter, lpp promoter, pLλ promoter, pRλ promoter, rac5 promoter, amp promoter, recA promoter, SP6 promoter, trp promoter, T7 promoter, pBAD promoter, Tet promoter, trc promoter, pepT promoter, sulA promoter, pol 11 (dinA) promoter, ruv promoter, uvrA promoter, uvrB promoter, uvrD promoter, umuDC promoter, lexA promoter, cea promoter, caa promoter, recN promoter and pagC promoter, etc.), and a ribosome binding site for the initiation of translation, transcription/translation termination sequence (e.g.: rrnB terminator). Besides, promoters operating in infarcted tissues may be included (e.g., hip promoter, ansB promoter, pflE promoter). In the meantime, a vector used for the present invention may be constructed by modifying a plasmid vector used in the art (e.g., pSC101, pGV1106, pACYC177, ColE1, pKT230, pME290, pBR322, pUC8/9, pUC6, pBD9, pHC79, pIJ61, pLAFR1, pHV14, pGEX series, pET series and pUC19, etc.), a phage vector (e.g., λgt4λB, λ-Charon, λΔz1 and M13, etc.) or viral vector (e.g., SV40, etc.).

In a preferred embodiment of the present invention, the delivered heterologous nucleic acid molecule may contain a leader sequence (or signal sequence) in order to promote the extracellular secretion of heterologous proteins expressed by the delivered heterologous nucleic acid molecule. The leader sequence may comprise a leader sequence of pelB, gene III, ompA, ompB, ompC, ompD, ompE, ompF, ompT, phoA and phoE, and so on, but not limited thereto.

Such advantages of the infarcted tissue-specific expression and secretion of heterologous proteins may be more strengthen by remote control of gene expression. As proved in the following examples, the infarcted tissue-specific expression of a heterologous protein may be remote-controlled using the infarcted tissue-targeting bacterium. In this case, the promoter operably linked to the heterologous nucleic acid molecule may be inducible promoter, and a preferred promoter may be lac, lacUV5, trp, tac, trc, rac, phoA, mgl, λ-P1, λ-Pr, T5, T7, tet, pBAD or SP6 promoter. For example, the expression of a heterologous protein may be induced by administrating L-arabinose, when pBAD promoter is operably linked to a polynucleotide encoding the heterologous protein.

In the meantime, the heterologous nucleic acid molecule delivered by the infarcted tissue-targeting bacterium of the present invention may be delivered by transposon-mediated chromosomal integration. In this case, a transposon plasmid may be used and the plasmid comprises a transposon in which a heterologous nucleic acid molecule is inserted, and then the transposon is integrated to bacterial chromosome. Exemplary transposons suitable for this purpose may include TO, Tn9, Tn10 and Tn5, but not limited thereto.

In a preferred embodiment of the present invention, the imaging agent delivered by the infarcted tissue-targeting bacterium may be a marker or a polynucleotide encoding the marker, when the marker is a protein. For instance, the marker may be a luminescent protein or a fluorescent protein, a marker protein for positron emission tomography (PET), a streptavidin or a receptor protein. In a more preferred embodiment, the marker may be a luminescent protein, a fluorescent protein or a marker for nuclear medicine imaging or MRI (magnetic resonance imaging). In a further preferred embodiment, the marker may be luciferase, green fluorescent protein (GFP), blue fluorescent protein (BFP), red fluorescent protein (RFP) or yellow fluorescent protein (YFP), herpes simplex virus thymidine kinase, dopamine receptor, somatostatin receptor, sodium-iodide transporter, transferrin receptor, ferritin or magA.

According to another aspect of the present invention, a pharmaceutical composition for treating infarction comprising (a) therapeutically effective amount of the drug delivery system of the present invention described above; and (b) at least one or more pharmaceutically acceptable carriers, wherein the drug delivery system comprises a pharmaceutical agent for treating infarction is provided.

According to another aspect of the present invention, a method for treating infarction comprising administrating the drug delivery system described above and a pharmaceutical agent for treating infarction delivered thereby to a subject.

An angiogenic factor used herein comprises all known angiogenic factors in the art, preferably may be VEGF (vascular endothelial growth factor), FGF (fibroblast growth factor), EGF (epithelial growth factor), angiogenin, angiotrophin, placenta growth factor, myogenic protein, angiogenic cytokine (e.g., interleukin-8, TNF-α), SIKVAV (SEQ ID NO: 5) peptide and neuropeptide Y. In addition, siRNAs or shRNAs inhibiting genes related to the degeneration of hypoxia inducible factor-1 (e.g., prolyl hydroxylase-2, PH2) may be included in the pharmaceutical composition. The sequence of the delivered heterologous nucleic acid molecule may be obtained from GenBank and EMBL. Expression construct comprising nucleotides sequence encoding the angiogenic factor may be explained by referring to the described above. For example, promoters and vectors used for the expression construct may be explained by referring to the sentences related to the infarcted tissue-targeting drug delivery system described above.

Since the pharmaceutical composition of the present invention uses the drug delivery system of the present invention as effective ingredients, common explains between the two are omitted in order to avoid excessive duplication.

The term used herein "effective amount" means the amount suitable for exhibiting therapeutic effect of the present invention described above.

The pharmaceutically acceptable carriers included in the pharmaceutical composition of the present invention are ones commonly used for drug formulation in the art, and comprise carbohydrate compounds (e.g., lactose, amylase, dextrose, sucrose, sorbitol, mannitol, starch and cellulose, etc.), Acacia gum, calcium phosphate, alginate, gelatin, calcium silicate, microcrystalline cellulose, polyvinyl pyrrolidone, cellulose, water, syrup, salt solution, alcohol, arabia gum, vegetable oil (e.g., corn oil, cotton seed oil, soy bean oil, olive oil, coconut oil, etc.), polyethylene glycol, methyl cellulose, methylhydroxy benzoate, propylhydroxy benzoate, talc, magnesium stearate and mineral oil, and so on, but not limited thereto. The pharmaceutical composition may further comprise a lubricant, a humectant, a sweetener, an emulsifier, a suspender, a preservative, etc. Suitable pharmaceutically acceptable carriers and additives are disclosed in Remington's Pharmaceutical Sciences (19th ed., 1995).

The pharmaceutical composition of the present invention is preferably administrated parenterally. Such a parenteral administration comprises intravenous (i.p.) injection, hydrodermic injection, intramuscular injection, intraperitoneal injection, etc.

Proper dose of the pharmaceutical composition of the present invention may vary according to various factors such as methods of formulating, administration methods, ages, weights, pathological states of patients, foods, administration time, administration routes, excretion rates, reaction sensitivities, etc and a skilled physician may determine and prescribe therapeutically effective dose for the required treatment or prophylaxis easily. In a preferred embodiment, proper daily dose may be 0.0001-100 mg/kg (weight). The daily dose may be administrated once a day or divided in several times.

The pharmaceutical composition may be manufactured in a single-dose formulation or enclosed in a multiple-dose vial by formulating using pharmaceutically acceptable carriers and/or excipients according to methods known in the art. In this case, the formulation may be a solution, a suspension or an emulsion in oily or aqueous media or may be extracts, powders, granules, tablets or capsules, and may further comprise a dispersion agent or a stabilizer.

One of advantages of the present invention is to terminate the therapy according to the present invention by injecting antibiotics. In this case, the exemplary antibiotics may be ciprofloxacin, amphicilin, gentamicin, carbenicillin, chloramphenicol, streptomycin, kanamycin, geneticin, neomycin or tetracyclin, but not limited thereto.

In another aspect of the present invention, a composition for imaging an infarcted tissue comprising (a) the above-described drug delivery system comprising an imaging agent; and (b) a pharmaceutically acceptable carrier is provided.

In another aspect of the present invention, a method of imaging an infarcted tissue comprising administrating the above-described drug delivery system and an imaging agent delivered thereby to a subject.

Since the composition for imaging an infarcted tissue of the present invention uses the above-described drug delivery system, common explanations between the two are omitted in order to avoid excessive duplication.

As for carriers, doses, administration routes and formulations of the composition for imaging an infarcted tissue of the present invention, the above-described explanations regarding the pharmaceutical composition of the present invention may be referred to.

The infarcted tissue-specific bacterium itself may be used for imaging an infarcted tissue. For example, if the infarcted tissue-specific bacterium is injected to a subject and then antibodies binding specifically the bacterium (preferentially labeled antibodies) are injected to the subject, the infarcted tissue may be imaged.

In a preferred embodiment of the present invention, the imaging agent delivered by the infarcted tissue-targeting bacterium may be a marker or a polynucleotide encoding the marker, when the marker is a protein. For instance, the marker may be a luminescent protein or a fluorescent protein, a marker protein for positron emission tomography (PET), a streptavidin or a receptor protein. In a more preferred embodiment, the marker may be a luminescent protein, a fluorescent protein or a marker for nuclide imaging or MRI (magnetic resonance imaging). In a further preferred embodiment, the marker may be luciferase, green fluorescent protein (GFP), blue fluorescent protein (BFP), red fluorescent protein (RFP) or yellow fluorescent protein (YFP), herpes simplex virus thymidine kinase, dopamine receptor, somatostatin receptor, sodium-iodide transporter, transferrin receptor, ferritin or magA.

Except that the marker protein itself produces signals for the detection thereof (e.g., when the marker protein is a fluorescent protein), the composition for imaging an infarcted tissue of the present invention may further comprises a marker-binding moiety which binds to the marker protein.

For instance, if the marker protein is streptavidin the marker-binding moiety will be biotin, and if the marker protein is a receptor the marker-binding moiety will be a ligand binding to the receptor specifically. Alternatively, antibodies against the marker protein may be used as the marker-binding moiety.

The method of imaging an infarcted tissue will be varied according to the maker.

For example, if the marker is made of magnetic substances, a magnetic resonance imaging (MRI) may be used; if the marker is a phositron emitting isotope, single photon emission computed tomography (SPECT) or phositron emission tomography (PET) may be used. MRI methods and apparatuses are disclosed in D. M. Kean and M. A. Smith, Magnetic Resonance Imaging: Principles and Applications (William and Wilkins, Baltimore 1986), U.S. Pat. Nos. 6,151,377, 6,144,202, 6,128,522, 6,127,825, 6,121,775, 6,119,032, 6,115,446, 6,111,410, and 602,891. PET imaging methods and apparatuses are disclosed in U.S. Pat. Nos. 6,151,377, 6,072,177, 5,900,636, 5,608,221, 5,532,489, 5,272,343, and 5,103,098. SPECT imaging methods and apparatuses are disclosed in U.S. Pat. Nos. 6,115,446, 6,072,177, 5,608,221, 5,600,145, 5,210,421, and 5,103,098. The documents are herein entirely incorporated by reference. If the marker is a luminescent, a fluorescent or a chemiluminescent molecule, optical imaging methods or spectroscopies may be used. These imaging methods are disclosed in U.S. Pat. No. 5,650, 135. In addition, the marker is one bound to barium sulfate or iodine which is X-ray imaging agents or a microbubble, radiography or ultrasonography may be used, respectively.

According to another aspect of the present invention, an angiogenic composition comprising (a) therapeutically effective amount of the drug delivery system described above; and (b) a pharmaceutically acceptable carrier, wherein the drug delivery system comprises at least one angiogenic factor or a polynucleotide encoding the angiogenic factor.

According to another aspect of the present invention, a method of inducing angiogenesis in a subject comprising administrating the drug delivery system described above and at least one angiogenic factor or a polynucleotide encoding the angiogenic factor delivered thereby to the subject.

The present invention includes all angiogenic factors known in the art. The exemplary angiogenic factor may be VEGF (vascular endothelial growth factor), aFGF (acidic fibroblast growth factor), bFGF (basic fibroblast growth factor), angiogenin, angiotrophin, EGF (epithelial growth factor) or IL-8.

Constitutions of expression constructs comprising the polynucleotide encoding the angiogenic factor may be explained by referring to the explanation described above. For instance, promoters and vectors used for the expression constructs may be explained by referring to the explanation of the drug delivery system of the present invention.

Diseases or conditions capable of being treated by the angiogenic composition of the present invention may be coronary artery occlusive disease, carotid artery occlusive disease, artery occlusive disease, peripheral artery disease, artherosclerosis; vascular hypertrophy (e.g., resulted from vascular surgery, balloon angioplasty or vascular stenting), thoromboangitis obliterans, thrombotic disease, vasculitis, myocardial infarction, ischemic heart failure, cardioplegia or ischemic disease (e.g., ischemic heart disease, ischemic myocardial infarction, ischemic heart failure, ischemic gastroenteritis, ischemic ocular disease, ischemic retinopathy, ischemic glaucoma, ischemic kidney failure, ischemic boldness, ischemic stroke or ischemic limb disease).

The angiogenic composition may be expressed as a pharmaceutical composition for treating the above-described diseases or conditions.

According to another aspect of the present invention, a drug delivery system (DDS) for penetrating blood-brain barrier (BBB) comprising obligatory anaerobic or facultative anaerobic bacterium is provided.

According to another aspect of the present invention, a method of delivering a pharmaceutical agent to a subject's brain through BBB comprising administrating a drug delivery system comprising an obligatory anaerobic bacterium or a facultative anaerobic bacterium and the pharmaceutical agent delivered thereby to the subject.

Since the DDS for penetrating BBB of the present invention uses the same bacterium as the DDS for delivering a pharmaceutical agent to an infarcted tissue, common explanations between the two are omitted in order to avoid excessive duplication.

As proven in the following examples, the DDS of the present invention injected intravenously passes through BBB surprisingly and migrates to the brain, especially infarcted brain.

There is no apparent result regarding diagnosing and treating of disease arisen in the brain. This is due to blood-brain barrier (BBB), a unique structure existing in brain blood vessel, consisting of astrocytes enclosing the blood vessel tightly. Thus, it has a role in selective passing through of substances essential for survival of neurons and blocking toxic substances thereby. However, the BBB blocks the penetration of drugs therethrough as well as various imaging agent for the diagnosis when brain diseases such as brain tumor, Alzheimer's disease and Parkinson's disease, etc. occur and this makes it difficult to develop technologies for treating or diagnosing brain diseases. For this reason, it is important to develop technologies capable of passing through BBB of imaging or treating agents. Up to date, methods for administrating pharmaceutical agent or imaging agents by disrupting BBB due to temporal chemical shock using drugs such as OX26 (anti-CD71 antibody), OX26-polyethylene glycol, mannitol or transferrin. Alternatively, methods of coadministrating the drug and pharmaceutical agents or imaging agents via chemical conjucation have been used (M. Gumbleton et al., 2006, *Journal of Drug Targeting*, 14: 191).

Thus, the present invention provides a new approach capable of delivering drugs into the brain, preferentially an infarcted brain tissue.

Advantageous Effects

Characteristics and advantages of the present invention are summarized as follows:
(i) The present invention provides an infarcted tissue-targeting bacterium primordially.
(ii) The present invention is applied to deliver pharmaceutical agent selectively to an infarcted tissue or image selectively the infarcted tissue.
(iii) The present invention is considerably advantageous compared with gene therapies using recombinant virus because treatments using the infarcted tissue-targeting bacterium of the present invention can be terminated by antibiotics.
(iv) Since the infarcted tissue-targeting bacterium of the present invention has high affinity and specificity toward myocardial infarction and brain infarction, undesirable transfection in other organs excepting infarcted heart and brain would be diminished.
(v) Gene expression using the infarcted tissue-targeting bacterium in infarcted tissues may be remote-controlled.

BRIEF DESCRIPTION OF DRAWINGS

The patent or application file contains at least one drawing executed in color. Copies of this patent or patent application publication with color drawing(s) will be provided by the Office upon request and payment of the necessary fee.

*S. typhimurium* (ΔppGpp) strain (S.t.+pLux) expressing lux ($2 \times 10^8$ CFU) was injected through the tail-vein into Sprague-Dawley rats with or without MI. Imaging signals were quantified in units of maximum photons (photons $s^{-1}cm^{-2}sr^{-1}$).

Figure 2:
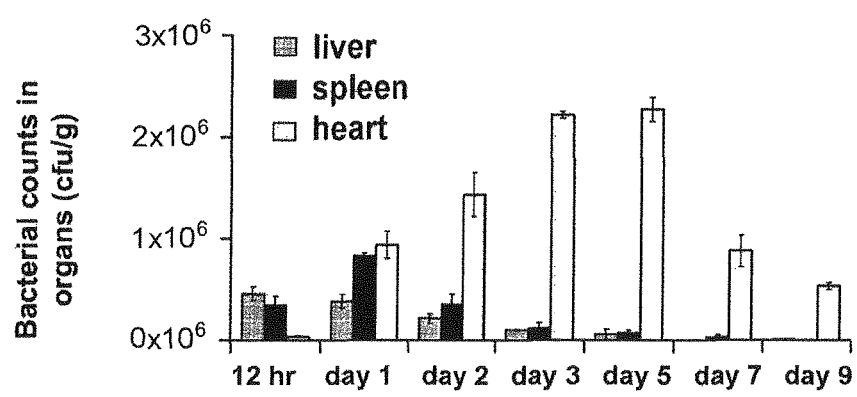

FIG. 2 is a graph showing number of bacteria in other organs (liver, spleen and heart) after intravenous injection of the *S. typhimurium* in MI rats (n=21).

Figure 3:
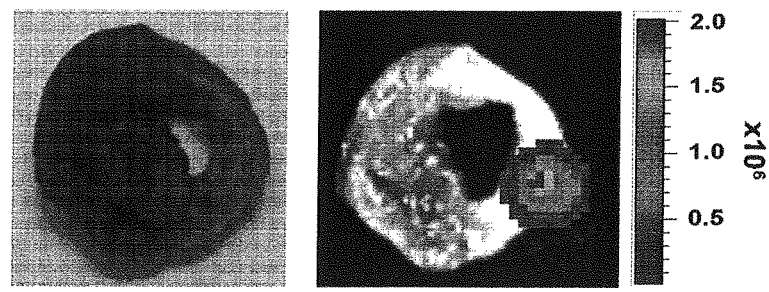

FIG. 3 is a cross-sectional image of a heart from MI rats at 5 days post inoculation (dpi) of *Salmonellae* injection. Bioluminescence imaging was performed for 30 seconds using cooled CCD camera (left panel). Thin slice (4 μm) cross-sections were prepared and then subjected to Masson's trichrome staining (right panel).

Figure 4:
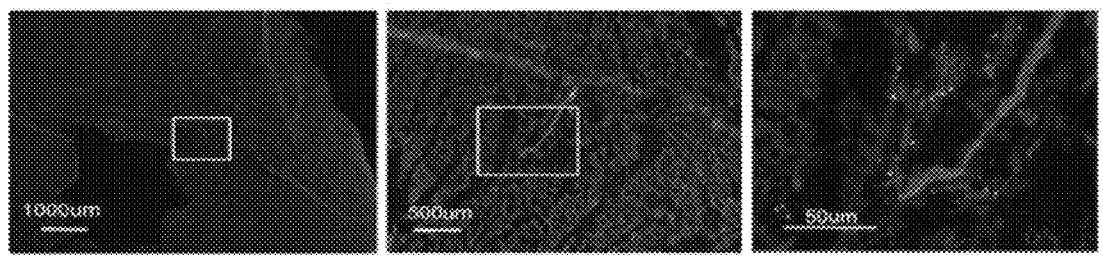

FIG. 4 is a photograph showing immunofluorostaining results in infarcted myocardium after injection of *S. typhimurium* (ΔppGpp) strains (S.t.+pGFP, 2 ×$10^8$ CFU) through tail-vein. Cardiac cross-sections of an MI rat were prepared at 5 dpi. The bacteria were stained in green color.

Figure 5:
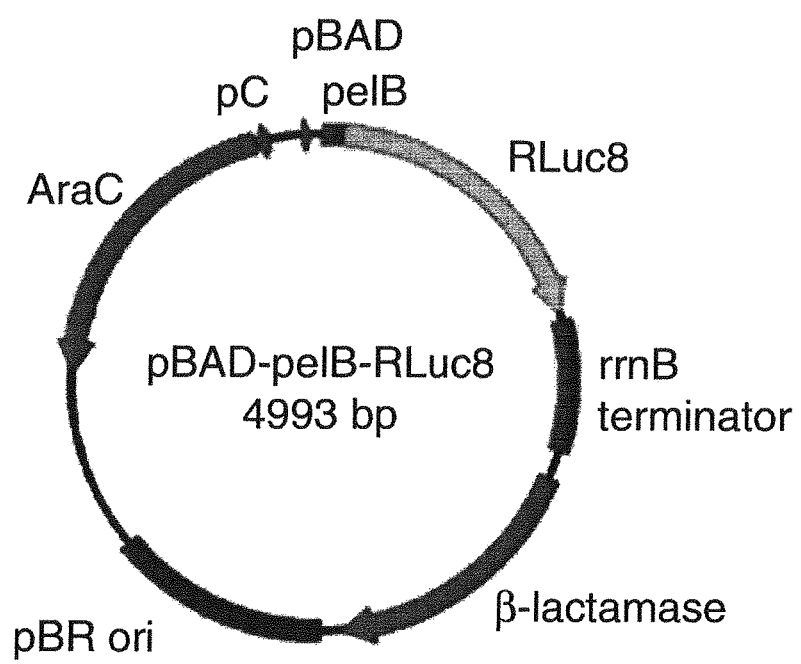

FIG. 5 is a plasmid map of a bacterial expression plasmid comprising a *Renilla* luciferase variant (Rluc8). *S. typhimurium* (ΔppGpp) strains were transformed with pBP-Ruc8 (S.t.+pBP-Rluc8).

Figure 6:
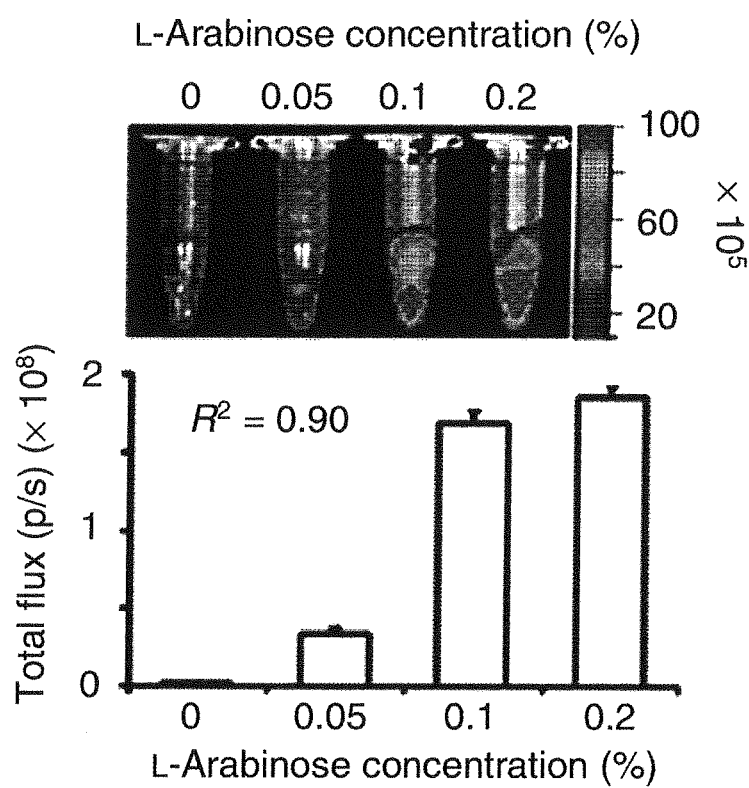

FIG. 6 is a series of bioluminescent images taken using cooled CCD camera immediately after 4 hours inoculation of bacterial cultures to which different concentrations (0 to 0.2%) of L-arabinose were added when they reached an $OD_{600}$ of 0.5 to 0.7

Figure 7:
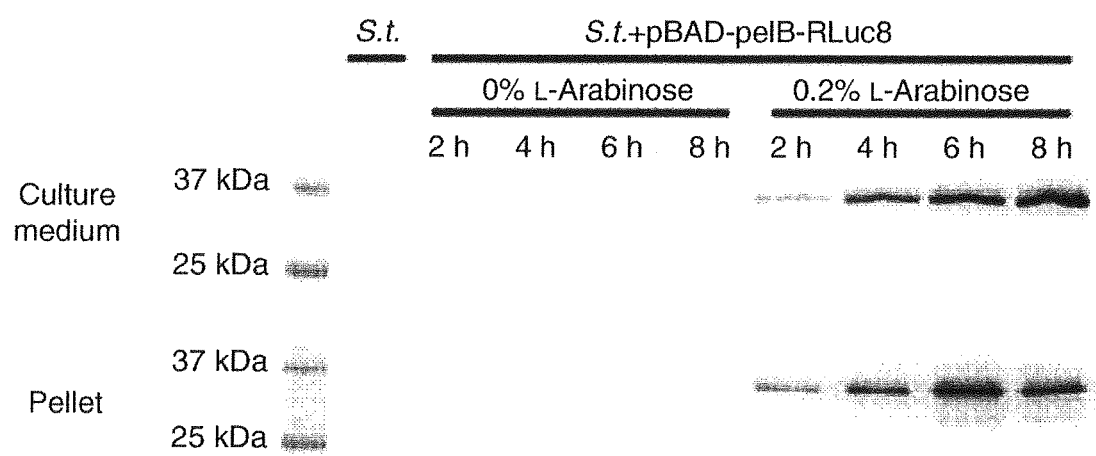

FIG. 7 is a photograph of western blotting analysis showing expression and secretion of Rluc8 protein (36.9 kDa) using anti-Rluc antibody. Bacterial pellets and culture medium were collected at the indicated times from 2 to 8 hours after treatment with or without 0.2% L-arabinose. The first lane represents *S. typhimurium* (ΔppGpp) carrying no plasmid (4 hours after fresh culture).

Figure 8:
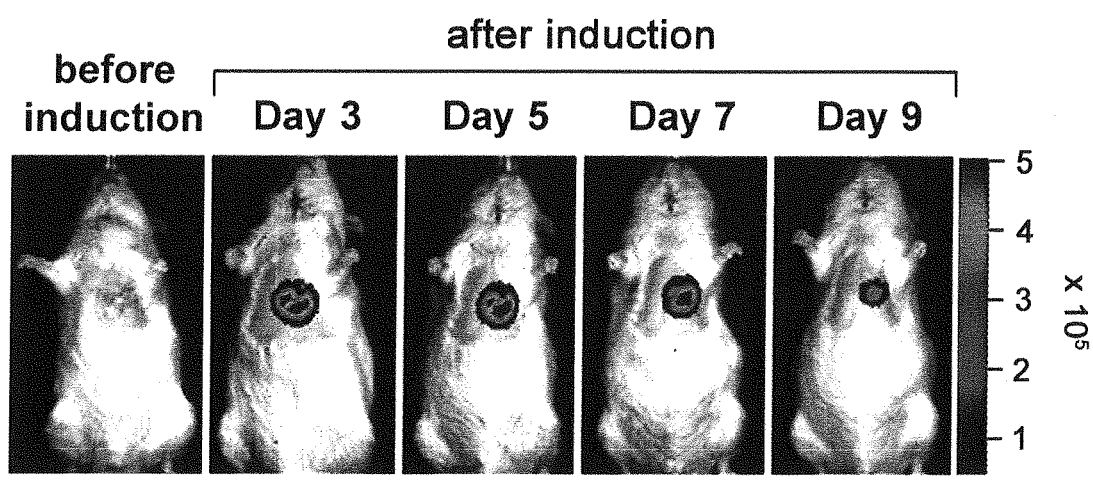

FIG. 8 is a series of in vivo bioluminescent images of MI rats after tail-vein injection of *S. typhimurium* (ΔppGpp) strain (S.t.+pBP-RLuc8, 2×10$^8$ CFU) into MI rats. The first image was obtained at 3 dpi, immediately before injection of L-arabinose. The other images were taken after 4 hours injection of L-arabinose (1.2 g). For imaging, 0.7 mg/kg body weight of coelenterazine (Biotiu, Calif.) was injected through tail vein into rats. Imaging signals were quantified in units of maximum photons (photons s$^{-1}$cm$^{-2}$sr$^{-1}$).

Figure 9:
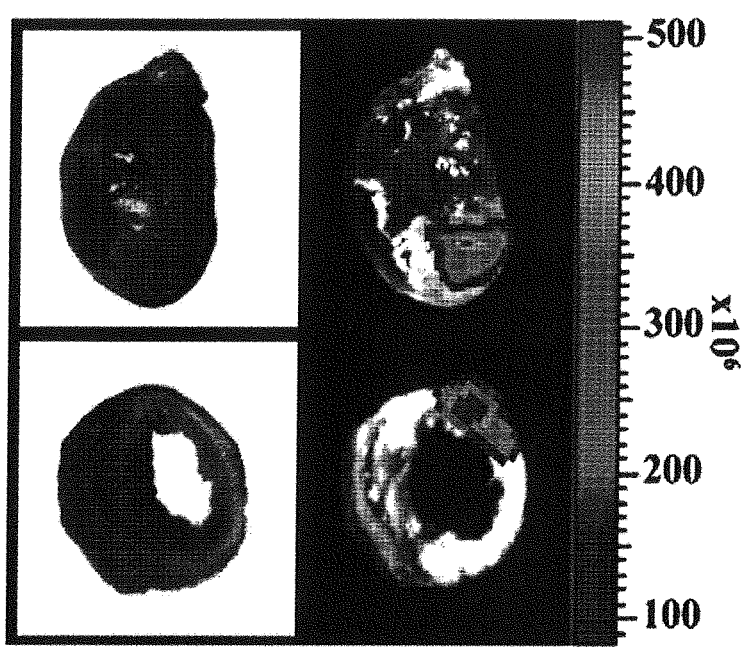

FIG. 9 is a series of bright field images and bioluminescence images of whole excised heart (top panel) and cross-sections thereof (bottom panel). Infarcted hearts were excised at 5 dpi. The hearts were subjected to triphenyltetrazolium chloride (TTC) staining (left panel) and bioluminescence imaging (right panel). Bright field images and bioluminescence images of whole excised hearts (top panel) and cross-sections thereof (bottom panel) are shown.

Figure 10:
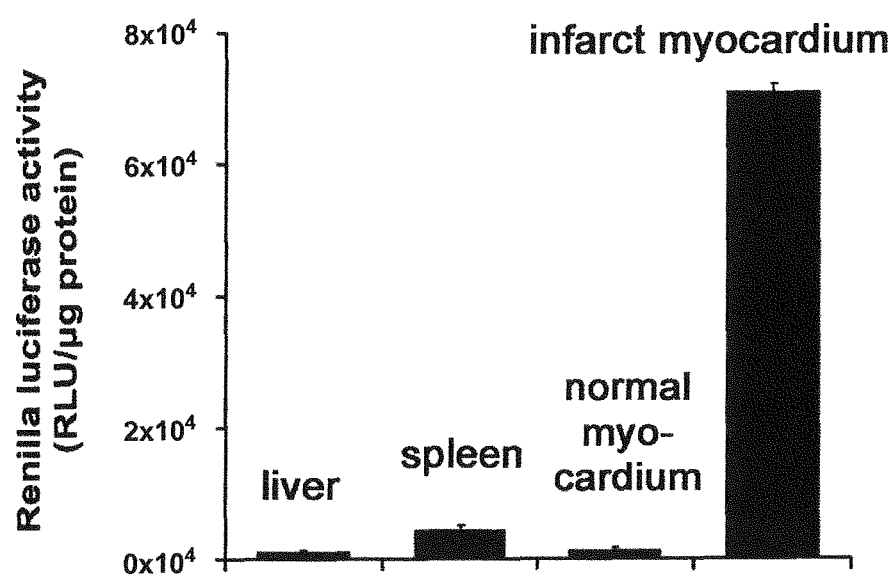

FIG. 10 is a graph representing bioluminescence in infarcted myocardium, noninfarcted myocardium, liver, and spleen, measured using a luminometer (Berthold) at 5 dpi. The Y-axis indicates relative light units (RLU) representing luciferase activity normalized to total protein concentration in tissue homogenates.

Figure 11:
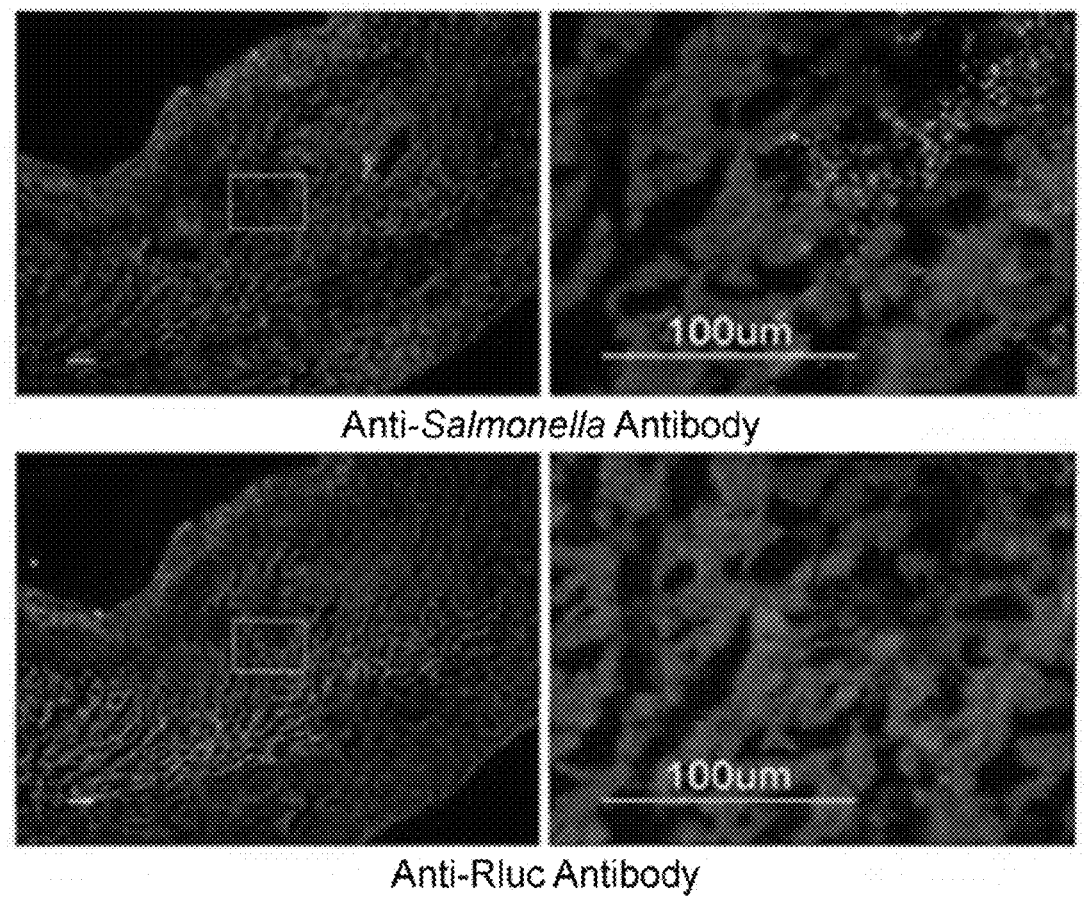

FIG. 11 is a series of immunofluorescence staining of infarcted hearts using anti-*Salmonella* antibody (top panel) and anti-Rluc antibody (bottom panel). The infarcted hearts were excised at 5 dpi. Top panel: cross-sectioned samples were reacted with primary antibody specific to *S. typhimurium*, and then the samples were reacted with FITC-conjugated secondary antibody. The samples were subjected to DAPI and Texas-Red counter-staining. Length of bars represent 100 μm. Bottom panel: cross-sectioned samples were reacted with anti-Rluc antibody (Chemicon) and then the samples were reacted with fluorecin isocyanate-conjugated secondary IgG antibody. Length of bars represent 100 μm.

Figure 12:
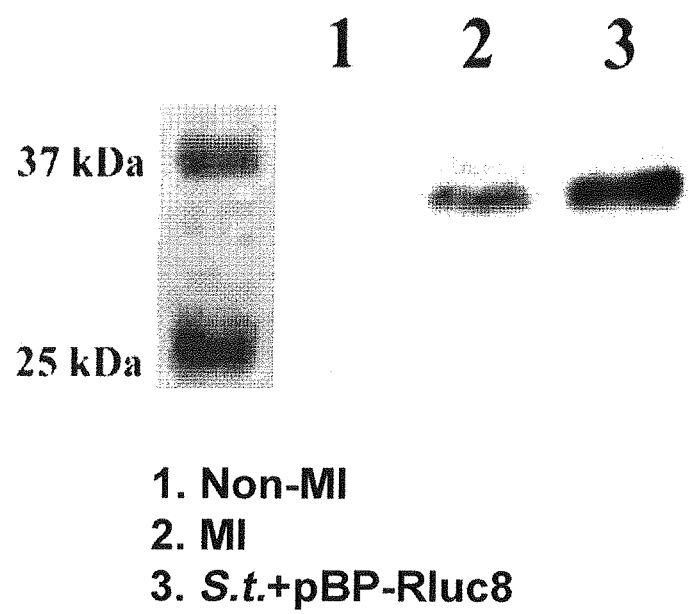

FIG. 12 is a photograph of western blotting analysis using anti-Rluc antibody in infracted myocardium (MI), contralateral normal myocardium (Non-MI) and *S. typhimurium* expressing Rluc8 (positive control). The expression of Rluc8 (36.9 kDa) was measured.

Figure 13:
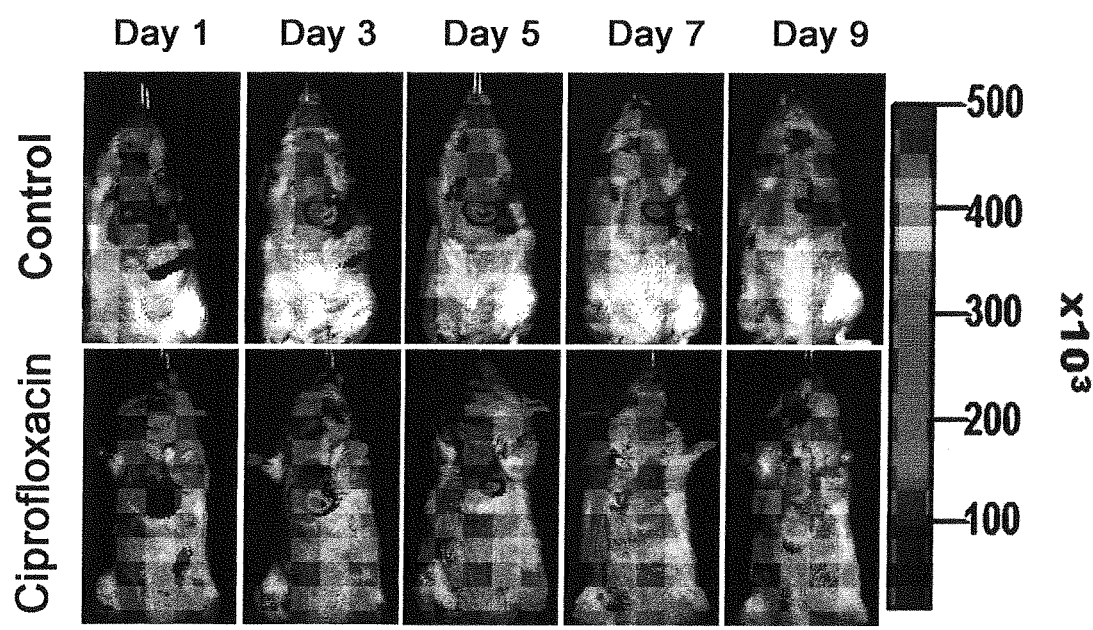
Figure 14:
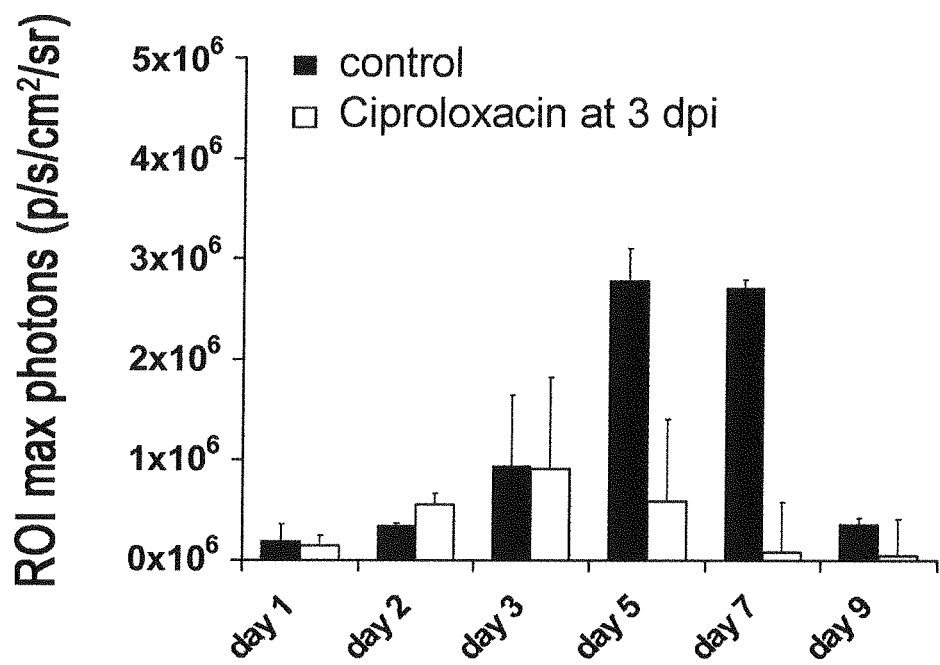

FIGS. 13 and 14 are results of clearance of bacterial infection by antibiotics. Ciprofloxacin (Sigma, 30 mg/kg/day) was administrated intraperitoneally twice a day to MI rats. The treatment was started at 3 dpi. Antibacterial activity was investigated by measuring bioluminescence in the rats.

Figure 15:
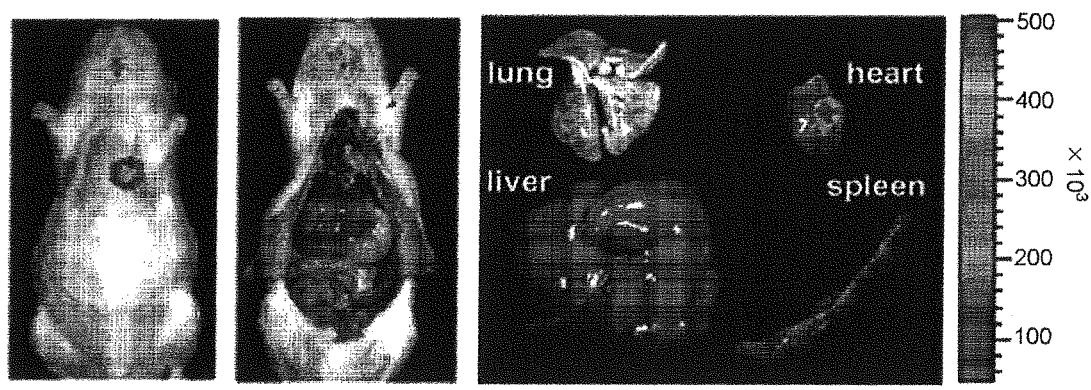

FIG. 15 is a series of images showing infarction-specific targeting by S.t.+pLux in MI rats. The rats were intraperitoneally injected with L-arabinose (1.2 g) at 3 dpi after tail-vein injection of S.t.+pBP-Rluc8 (2×10$^8$ CFU). Four hours after the injections of L-arabinose, rats were sacrificed and bioluminesce was imaged in whole bodies and isolated organs. For the imaging, rats were injected with 0.7 mg/kg body weight of coelenterazine (Biotium, Calif.) through tail vein. Imaging signals were quantified in units of maximum photons (photons s$^{-1}$cm$^{-2}$sr$^{-1}$).

Figure 16:
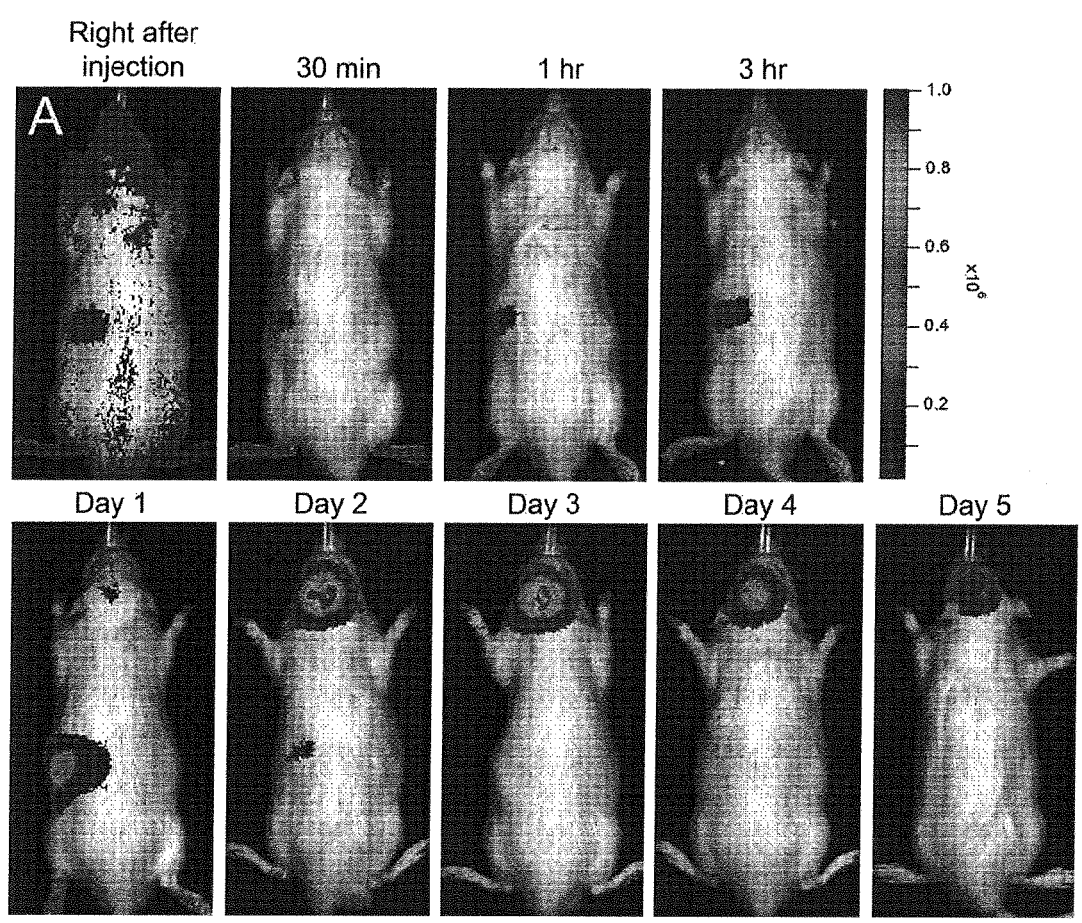

FIG. 16 is a series of images showing distributions of *Salmonellae* in rat models at the indicated times by acquiring gross necropsy images using cooled CCD camera (IVS-100, Xenogen-Caliper).

Figure 17:
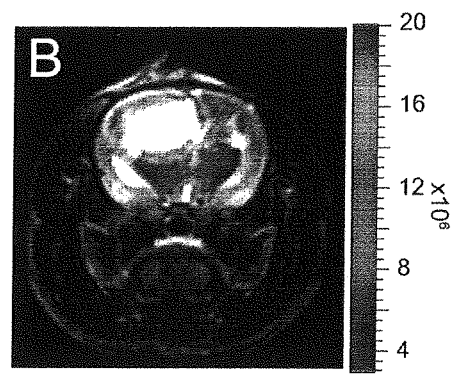

FIG. 17 is a photograph of an excised brain at 3 dpi from a model rat for observing more precise location of *Salmonellae*.

Figure 18:
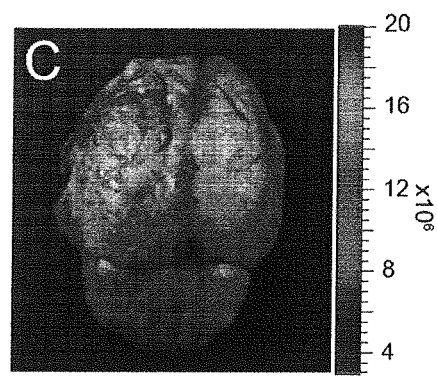

FIG. 18 is a photograph of a model rat brain using cooled CCD camera.

Figure 19:
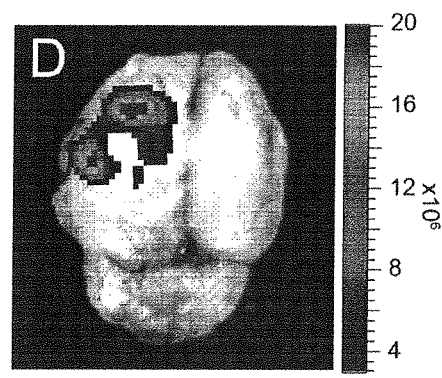

FIG. 19 is a T2-weighted MR image or a model rat brain.

Figure 20:
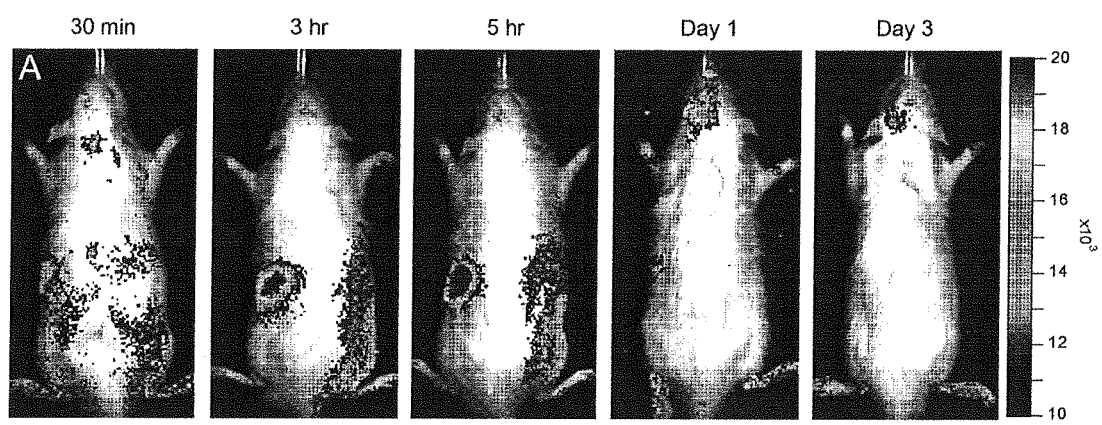

FIG. 20 is a photograph showing location of *Salmonellae* injected into an ICH (intracranial hemorrhage) rat model. The distribution of *Salmonellae* was determined by acquiring gross necropsy images at the indicated times using cooled CCD camera.

Figure 21:
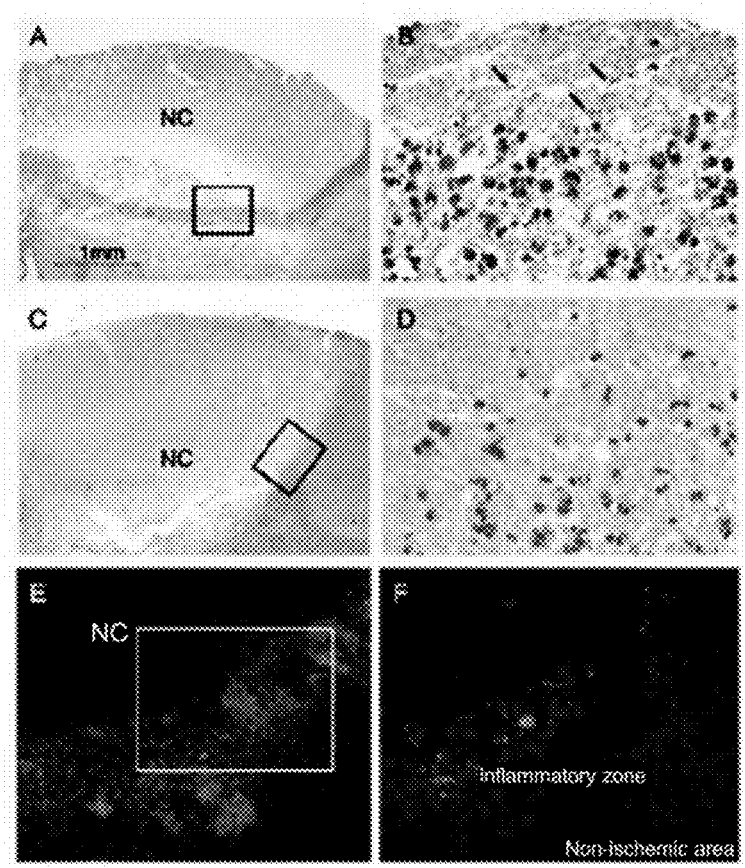

FIG. 21 is a series of images showing histological analysis of infarcted region of brain cross-sections of rats having cerebral ischemic infarction at 3 dpi. According to H&E staining, accumulation of inflammatory cells due to infiltration of basophiles at the boundary of infracted region (between necrotic core (NC) and normal brain tissue) was shown and this was observed as dark bands (dark arrows in A and C) when injected with *Salmonellae* (A and B) or not (C and D). Panels E and F represent confocal microscopic images of excised brain after injection of *Salmonellae* expressing GFP (green fluorescent protein) through tail vein. Panels B, D and F represent magnified images of boxes of A, C and E, respectively.

Figure 22:
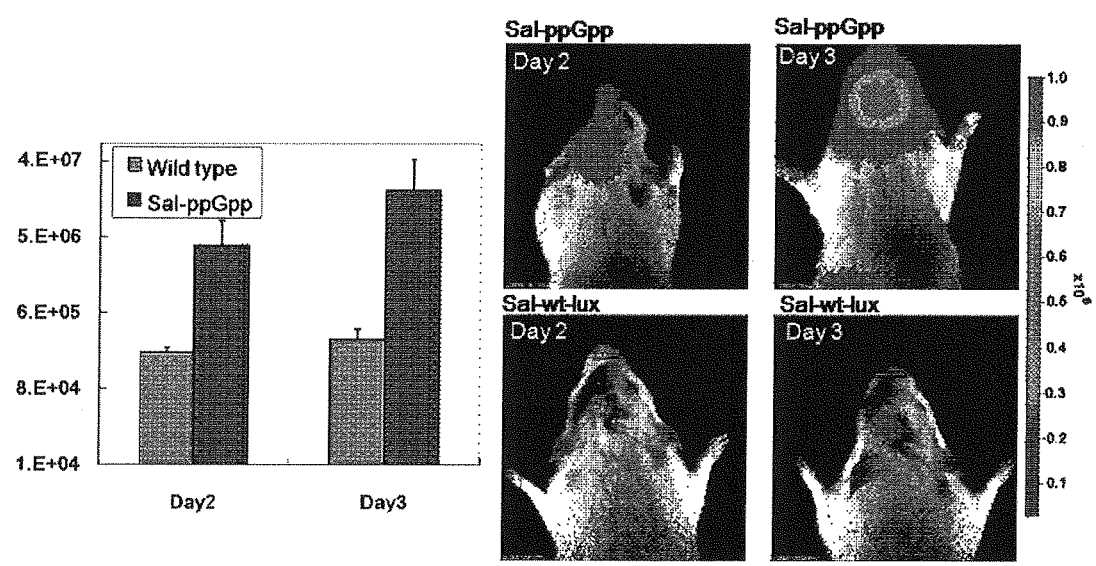

FIG. 22 represents targeting of ppGpp mutant (Sal-ppGpp) or wild-type *S. typhimurium* to cerebral ischemic region of rats. *Salmonellae* (5×10$^8$ CFU) expressing lux were intravenously injected. At 2 and 3 dpi, images were acquired using a cooled CCD camera (right panel). Bioluminescences at 2 and 3 dpi emitted from bacteria were compared (left graph).

Figure 23:
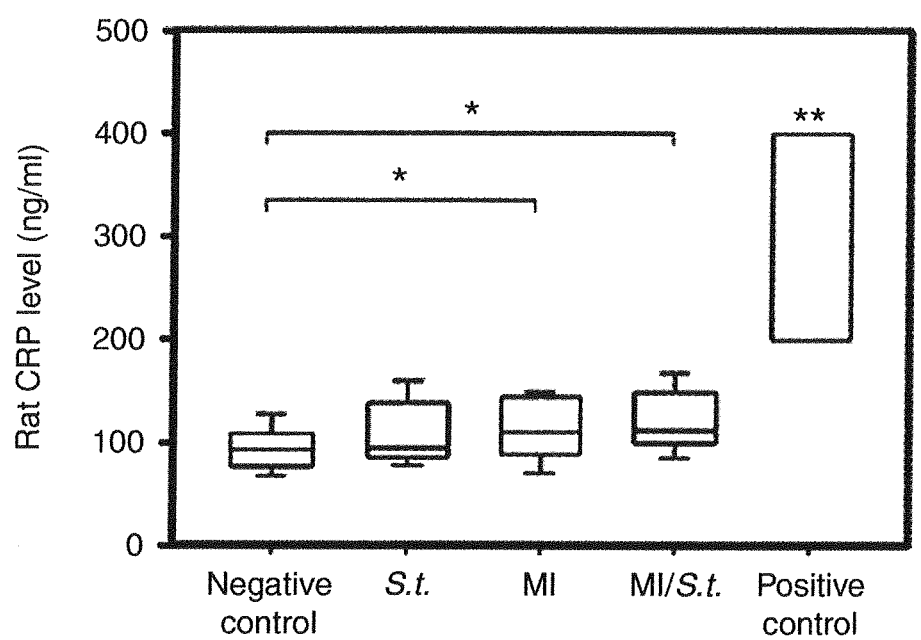

FIG. 23 is a graph showing toxicological analysis of attenuated *S. typhimurium* in rats. CRP level was measured in order to investigate systemic or topical inflammation after intravenous injection of attenuated *S. typhimurium* (ΔppGpp). Plasma CRP levels in sham operated and MI rats (n=3 each) before and after the injection of *Salmonellae* (2×10$^8$ CFU) were measured at 1 and 5 dpi. The results are expressed as averages of CRP levels at 1 and 5 dpi. Rats (n=3) were intravenous injected with lipopolysaccharide (LPS, 5 mg/kg for 3 minutes) as positive control, and blood was collected 4 hours after injection. Negative control indicates sham operated rats; S.t., sham operated rats with bacterial injection; MI, MI rats without bacterial injection; MI/S.t., MI rats with bacterial injection; positive control, LPS injected rats. The closest borders of boxes to 0 represent the 25th percentile; lines in boxes represent averages; the farthest borders of boxes from 0 represent the 75th percentile. Error bars over or below boxes represent the 10th and 90th percentiles. *P=0.035; **P<0.01.

Figure 24:
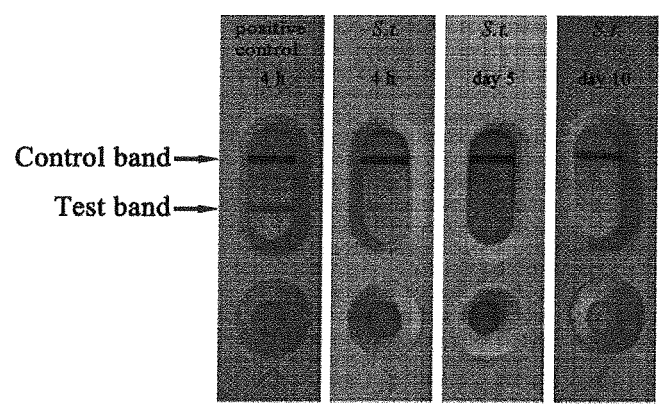

FIG. 24 is an immunochromatogram showing systemic toxicological analysis regarding injection of *S. typhimurim* (ΔppGpp). PCT levels in rat plasmas at 4, 5 and 10 dpi after infection of bacteria (2×10$^8$ CFU) were analyzed using immunochromatography. Rats (n=3) were intravenously injected with LPS (5 mg/kg, for 3 min) as positive control. Blood was collected 4 hour after injection.

BEST MODES

Hereinafter, the present invention will be described by examples. Purpose of these examples is only for explaining the present invention in detail, and it is obvious to a skilled person in the art that the scope of the present invention is not limited thereto.

EXAMPLES

I. Selective Targeting to Myocardial Infarction
  Experimental Procedures
  Plasmid
  An expression plasmid pBAD-peIB-RLuc8 (pBP-Rluc8) has been previously described[23]. More particularly, Rluc8, particular variant of *Renilla* luciferase was constructed among 8 preferential combinations and was inserted into pBAD/Myc-His A plasmid (Invitrogen, Carlsbad, Calif.). And then final plasmid constructed by linking polynucleotides corresponding to peIB leader sequence and N-terminal of luciferase.

Bacterial Strains

*S. typhimurium* strain (ΔppGpp) SHJ2037 (relA::cat, spoT::kan) has been previously described by the present inventors[30]. *S. typhimurium* strain (ΔppGpp) SHJ2037 having deficiency in ppGpp production due to deletions of re/A and spoT gene was deposited in the Korean Collection for Type Culture in Korea Research Institute of Bioscience and Biotechnology, which is an International Depository Authority under accession number of KCTC 10787BP. *Salmonellae* were grown in Luria-Bertani broth (LB) medium (Difco Laboratories) containing 50 μg/ml of kanamycin with vigorous aeration at 37° C. For the bioluminescence imaging, the bacterial luciferase gene (lux) from *S. typhimurium*-Xen26 (Xenogen-Caliper) was transduced into strain SHJ2037 by P22HT int transduction[31]. The strain was cultivated in LB medium containing 50 μg/ml of kanamycin. The SH2037 strain was transformed with pBAD-peIB-Rluc8 using electroporation. And then colonies growing on LB agar plates containing 50 μg/ml of ampicillin.

Animal Models

Eight-week old, male Sprague-Dawley (SD) rats (250-260 g; OrientBio, Kyunggi-do, Korea) were used. Animal care, all experiments and euthanasia were performed in accordance with protocols approved by the Chonnam National University Animal Research Committee and the Guide for the Care and Use of Laboratory Animals published by the National Institutes of Health (NIH publication 85-23, revised 1985). Rats were anesthesized with isoflurane (2%) during imaging or ketamine hydrochloride (100 mg/kg) and xylazine hydrochloride (2.5 mg/kg) during operating. Anesthesized rats breathed under positive pressure using a rodent respirator. Left thoracotomy was performed at the 4th intercostal space and the pericardium was opened. Left coronary artery was occluded for 30 min within myocardium between left arterial appendage and right ventricular outflow tract using curved needle and 5-0 silk and then the occlusion was relieved. Six hours after surgery, MI rats were injected through the lateral tail-vein with a fresh culture of *Salmonellae* ($2 \times 10^8$ CFU) resuspended in 100 μl of 1×PBS after anesthesized in an isofluorane chame. Also sham-operated rats were injected with the bacteria at the same dose.

Enumeration of Attenuated *S. Typhimurium*

At specific times indicated in FIG. 2, rats were euthanized and placed in 70% ethanol for 3 minutes. Organs such as heart, liver, and spleen were removed, and placed individually into sterile tubes containing PBS at 4° C., and weighed. Samples were transferred to sterile homogenization tubes, homogenized, and returned to the original tubes for the preparation of serial dilutions with PBS. Agar plates containing kanamycin (50 μg/ml) were inoculated with the homogenate, and the plates were incubated overnight at 37° C. Colonies were counted and bacterial load was expressed as CFU/g tissue.

Optical Bioluminescence Imaging of Rluc8 Expression in MI Rata

For imaging bacterial bioluminescence, anesthesized live rats were placed in light-blocking chamber of IVIS 100 (Xenogen-Caliper) equipped with cooled CCD camera. Photons emitted from luciferase-expressing bacteria were collected and integrated for 1 min. Pseudo color images representing counted photons were overayed on bright optical images of rats using living image software version 2.25 (Xenogen-Caliper, Hopkinto, Mass.). Region of interest (ROI) was selected based on signal intensity. Imaging signals were quantified in units of maximum photons per second per centimeter square per steradian ($ps^{-1}cm^{-2}sr^{-1}$) within the region of interest (ROI) maintaining the ROI uniformly. In order to activate pBAD promoter in the bacteria, 1.2 g of L-arabinose dissolved in PBS was injected intraperitoneally (i.p.) into rats. As negative control, 1 ml of saline was i.p. injected i.p. into bacteria-infected MI rats (n=3). Before imaging, coelenterazine (Biotium, Calif.) dissolved in methanol (stock solution of 2 mg/ml) was injected intravenously (i.v.) at a dose of 0.7 mg/kg body weight in a final volume of 200 μl.

Measurement of *Renilla* Luciferase Activity in Organs

After imaging, rat organs (spleen, liver, and heart) were excised and homogenized in lysis buffer (4 ml/g; Promega, Madison, Wis.), and subjected to five cycles of freezing and thawing. After centrifugation at 13,000 rpm for 3 minutes at 4° C., the supernatants were assayed for *Renilla* luciferase activity. Briefly, 20 μl of sample were mixed with 100 μl of 1× *Renilla* luciferase assay reagent (Promega) in a 96-well plate (Nunc), and luciferase activity was quantitated immediately using a luminometer (Microlumat Plus LB96V, Berthold, Wildbad, Germany). Light intensity was represented as relative light unit and normalized to protein concentration as Bradford assay.

Western Blot Analysis

Same quantities of bacterial cells were collected after addition of 0% or 0.2% L-arabinose. Bacterial cell extracts (40 μg) were analyzed by electrophoresis and blotted, as previously described[30,32]. Blots were reacted with a mouse anti-RLuc monoclonal antibody (1:5,000 dilution, Chemicon, Temecula, Calif.), HRP-conjugated goat anti-mouse IgG (1:80,000 dilution, Santa Cruz, Calif.) and luminol reagent (Santa Cruz).

Histological Analysis

Determination of Ischemic Tissues

Rats were sacrificed and hearts were isolated therefrom and then washed with 1×PBS several times. Cross-sections (0.5 mm thickness) were embedded in 0.4% of 2,3,5-triphenyltetrazolium chloride (TTC, Fluke, Sigma, India) solution for 20 min at 37° C.

Immunofluorescence Staining

Heart samples fixed with 4% paraformaldehyde were placed in PBS containing 30% sucrose and freezed at −80° C. After freezing, the samples were reacted with rabbit anti-*Salmonella* antibody (1:50, AbD Serotec, Oxford, UK) or mouse monoclonal anti-Rluc antibody (1:100, Chemicaon, Temecula, Calif.), and then the samples were reacted with FITC-rabeled anti-rabbit IgG (1:100, Serotec) or FITC-rabeled goat anti-mouse IgG (1:100, Santa Cruz, Calif., USA). Next, the samples were imaged using confocal microscopy.

Toxicological Analysis of Attenuated *S. Typhimurium*

Systemic or topical inflammation and infection after administration of *S. typhimurium* strain (ΔppGpp) were determined by measuring the levels of CRP in rat plasma, using a rat CRP enzyme-linked immunosorbent assay kit (Life Diagnostics, West Chester, Pa.) and PCT (Brahms PCT-Q; Hennigsdorf, Germany).

Clearance of Bacterial Infection by Antibiotics

For terminating bacterial infection, ciprofloxacin (30 mg/kg/day) was injected i.p. twice a day. The injection of ciprofloxacin was started at 3 dpi after injection of S.t.+pLux ($2 \times 10^8$ CFU) through tail vein. Final concentration of ciprofloxacin solution was 1.6 mg/ml.

Statistical Analysis

Differences in one factor between two groups were determined using analysis of variance (ANOVA) with a post-hoc test or Kruskal-Wallis analysis of variance (for nonparametric data). A P value of <0.05 was considered statistically significant for all analyses. Data are expressed as means±standard deviation (SD).

Experimental Results

Selective Localization of Attenuated S. Typhimurium in the Infarcted Myocardium

Figure 1:
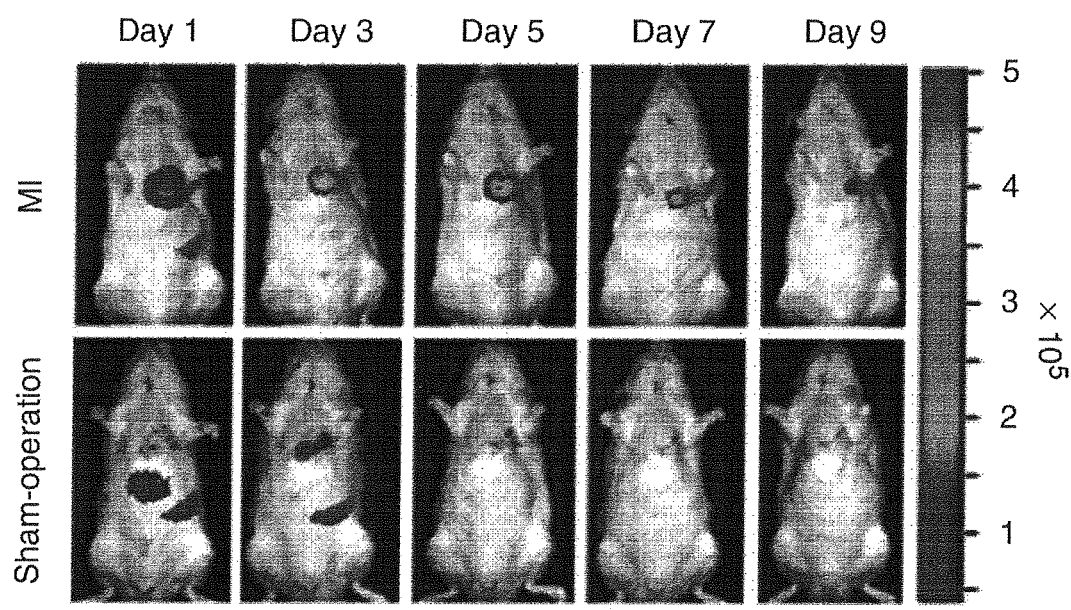
FIG. 1 is a series of bioluminescent imaging results in sham operated and MI rats.

Firstly, spatial distribution of S. typhimurium strain in rat myocardium infarction (MI) model. MI model was prepared by surgical occlusion of left coronary artery. An attenuated strain of S. typhimurium deficient in the production of ppGpp was used: LD50 of this attenuated strain is $10^5$ fold higher than that of wild-type strain[21]. After constructing a bioluminescent S. typhimurium strain whose chromosome has lux operon, sham operated rats (n=5) and MI rats (n=10) was injected with the strain ($2\times10^8$ CFU) through tail vein. Then, gross necropsy images were acquired using cooled CCD camera. Bioluminescent signal was detected in the heart of MI rats at 1 day post inoculums (FIG. 1, top panel). Three days after injection, bioluminescence persisted in the heart but was no longer detected in spleen. Serial monitoring of the rats revealed an initial increase in cardiac bioluminescence up to 5 dpi, followed by a progressive decline in signal intensity. This decline likely reflected a decrease in the number of bacteria in the heart, presumably due to host immune response. In sham operated rats, bioluminescence was detected only in the spleen and liver at 1 and 3 dpi (FIG. 1, bottom panel), reflecting the reticuloendothelial nature of these organs. To correlate the imaging data with bacterial load in the heart, spleen, and liver, number of bacteria (CFUs) in the organs of MI rats (n=21) was counted. Early after injection (12 hours), bacterial load was found primarily in the spleen ($3.5\times10^5$ CFU/g) and liver ($4.6\times10^5$ CFU/g), but bacteria existing in the heart ($3.6\times10^4$ CFU/g) were at low level (FIG. 2). After 24 hours, however, the number of bacteria in myocardial tissue increased dramatically, reaching a maximum at 3 and 5 dpi ($2.2\times10^6$ CFU/g and $2.3\times10^6$ CFU/g, respectively), whereas the bacterial burden in the liver and spleen declined over the same period of time to undetectable levels. The numbers of bacteria were monitored continuously up to 9 dpi, and no bacterial increase was found in the liver and spleen, suggesting that the bacteria do not recolonize in the liver and spleen after being released from the heart. Analysis of the myocardial tissue sections from the MI rats revealed that bioluminescence was specifically located in the anterolateral wall of left ventricular (FIG. 3, right panel), and this perfectly corresponds to scar tissue of the same region revealed by Masson's trichrome staining (FIG. 3, left panel). In order to analyze location of bacteria precisely, MI rats were injected with ΔppGpp strain expressing green fluorescent protein (GFP) through tail vein and excised myocardiums were analyzed using confocal microscopy. GFP-expressing bacteria were observed in infarcted myocardial tissue (FIG. 4), but not in contralateral normal myocardial tissue. Imaging and histological analyses definitely shows intravenously injected bacteria colonize selectively in infarcted tissues.

Remote-control of Attenuated S. Typhimurium by the Induction of Bacterial Gene Expression and the Secretion of Protein In Vitro and In Vivo A bacterial expression plasmid containing Renilla luciferase variant (Rluc8)[22,23] was constructed to direct protein secretion into the bacterial periplasm. pelB leader sequence[24] was fused to N-terminus of the luciferase and a 6×His tag was fused to C-termus thereof. The pelB leader sequence consisting of the first 22 codons of the gene for pectate lyase B from Erwinia cartovora directs protein secretion into the bacterial periplasm before being cleaved to mature protein. In order to express a gene selectively in ischemic myocardium, pBAD promoter from E. coli arabinose operon (FIG. 15) was used. The induction of Rluc8 expression in S. typhimurium transformed with pBAD-pelB-Rluc8 (pBP-Rluc8) vector was investigated. Various light signals were found when various concentrations of L-arabinose were added to cultured bacterial cells. However, no light signal was detected in the absence of L-arabinose (FIG. 6). Western blot analysis using anti-Rluc antibody revealed that a 36.9 kDa protein was expressed in the pellet and supernatant of strain containing pBP-Rluc8 only in the presence of L-arabinose (0.2%), suggesting that Rluc8 protein expresses selectively and is secreted from bacteria (FIG. 7).

Selective Expression and Secretion of Proteins in Infarcted Myocardium by Attenuated S. Typhimurium Subsequently, MI rats (n=12) were injected i.v. with S. typhimurium (ΔppGpp) strain carrying pBP-RLuc8 ($2\times10^8$ CFU). L-arabinose was administered on 3 dpi to induce RLuc8 expression because previous results of imaging and bacterial counting showed that the number of bacteria declined in the liver and spleen significantly, while reaching a maximum in infarcted myocardium at 3 dpi (FIG. 1 and Table 1). The expression of RLuc8 was monitored using cooled CCD camera (IVIS-100, Xenogen-Caliper) after i.p. injection of L-arabinose and the luciferase substrate coelenterazine (after 3 dpi). Bioluminescence was detected from 3 to 9 dpi, which is whole length of the experimental period (FIG. 20) peaking at 5 dpi and declining thereafter, most likely due to the decreased bacterial cell number (Table 1). Notably, light signal from the cardiac region was observed only after the injection of 1-arabinose, and no bioluminescence was detected in the spleen or any other organs. These results were verified by acquiring CCD images of gross necropsy and isolated organs (FIG. 15). It is supposed that Salmonellae may be eliminated from organs other than the heart easily by host immune system when the Rluc8 expression is in induced. In addition, as shown in FIG. 1, light signal from myocardium after 7 dpi declined. Using cooled CCD camera, cross-sected heart at 5 dpi was analyzed and strong bioluminescence was detected from the anterolateral wall of the myocardium (FIG. 21, top panel). Cross-sectional image of bacterial signal and TTC staining of infarcted tissue corresponded to each other; bioluminescence was detected only in the anterolateral wall of the myocardium (FIG. 21, bottom panel). Quantitation of RLuc8 activity in various tissues showed that luciferase activity was significantly higher in the infarcted myocardium than in the contralateral normal myocardium (>50-fold higher, P<0.001) or in any other organ (P<0.001, FIG. 22). Additional experiments were carried out in order to verify the selective expression of RLuc8 in the infarcted myocardium (FIG. 23). According to microscopic observation, bacteria were localized mainly in the infarcted region of myocardium (FIG. 23, top panel). Immunostaining with anti-Rluc antibody revealed that Rluc8 protein located in the infarcted myocardium (FIG. 23, bottom panel). The above result was verified with western blot assay using anti-Rluc antibody showing that 36.9 kDa of protein exists in the infarcted myocardium but not in contralateral normal RLuc8 (FIG. 24). Taken together, these results suggested a feasibility of engineered bacteria to selectively express a gene of interest in the infarcted tissue.

TABLE 1

|  | 12 h | Day 1 | Day 2 | Day 3 | Day 5 | Day 7 | Day 9 |
| --- | --- | --- | --- | --- | --- | --- | --- |
| Heart | $4.15 \times 10^4 \pm 1.29$ | $7.10 \times 10^5 \pm 1.33$ | $1.49 \times 10^6 \pm 0.22$ | $2.24 \times 10^6 \pm 1.29$ | $2.57 \times 10^6 \pm 0.29$ | $8.75 \times 10^5 \pm 1.54$ | $5.29 \times 10^5 \pm 1.29$ |
| Spleen | $1.43 \times 10^6 \pm 0.96$ | $6.44 \times 10^5 \pm 1.63$ | $3.56 \times 10^4 \pm 0.94$ | $6.20 \times 10^2 \pm 0.62$ | 0 | 0 | 0 |
| liver | $2.10 \times 10^5 \pm 1.18$ | $4.65 \times 10^5 \pm 0.70$ | $2.12 \times 10^3 \pm 0.45$ | 0 | 0 | 0 | 0 |

Table 1 represents the quantification of *S. typhimurium* (ΔppGpp) strain in organs after i.v. injection in rat myocardial infarction model. Numbers of Table 1 represent colony forming units in 1 g of tissue (CFU/g tissue).

Clearance of Bacterial Infection by Antibiotics

MI rats infected by *Salmonella* ($2 \times 10^8$ CFU) were injected with ciprofloxacin (30 mg/kg/day, Sigma) twice a day after acquiring biolumescence images at 3 dpi. Bioluminescence signal from the heart decreased and was eliminated after 5 dpi, suggesting that bacteria were extincted by antibiotics (FIG. 4).

Analysis of Toxicity of Bacterial Infection and Clearance

The therapeutic administration of live bacteria often raises concerns of potential toxicity. Thus, the present inventors sought to characterize the acute and short-term toxicity of attenuated *S. typhimurium* (ΔppGpp) strain following i.v. injection into rats (n=5 for each group) by monitoring the levels of plasma C-reactive protein (CRP) and procalcitonin (PCT) (FIG. 23 and FIG. 24). The CRP is an acute phase protein that is elevated in plasma and serum as a result of injury, infection, or disease. The PCT is a sensitive and specific marker for bacterial infection, particularly sepsis. The plasma levels of CRP in sham operated and MI rats were 95.2±20.7 ng/ml and 115.7±28.5 ng/ml, respectively (P=0.035), which indicated that local inflammatory reactions were induced following surgical induction of MI in rats. However, there were no significant differences in plasma CRP levels after i.v. injection of *S. typhimurium* (ΔppGpp, $2 \times 10^8$ CFU) into MI or sham operated rats (P=0.358 for MI rats, P=0.12 for sham operated rats). Plasma PCT was also undetectable after administration of *S. typhimurium* (ΔppGpp) strain (FIG. 24, a positive test band indicates a plasma PCT level above 0.5 ng/ml). In addition, the present inventors examined whether or not bacterial localization in myocardium would give rise to further myocardial damage. The size of infarcted area as assessed by TTC staining was compared in MI rats with (*S. typhimurium* (ΔppGpp) strain) or without (PBS) bacterial infection. There were no significant differences in the infarct size between two groups as determined at 1 (P=0.540), 3 (P=0.189), and 7 dpi (P=0.098). These results strongly suggest that i.v. administration of attenuated *S. typhimurium* (ΔppGpp) strain does not lead to serious local or systemic inflammatory reactions.

Discussion

In summary, the present inventors demonstrated for the first time that attenuated *S. typhimurium* (ΔppGpp) strain exhibits a specific tropism for infarcted myocardial tissue and can be engineered to secrete a target protein into the infarcted myocardium. This novel finding suggests that the *Salmonellae* can be exploited as a vehicle for the delivery of therapeutic proteins in MI patients. The engineered *S. typhimurium* used in the present invention exhibited several useful features: i) an intrinsic tropism for infarcted myocardium, as demonstrated by bioluminescence imaging of reporter gene expression; ii) inducible gene expression and secretion of proteins into the infarcted myocardium; and (iii) confined gene expression in infarcted myocardium without spillover to noncardiac tissue.

Specific affinity to myocardial infarction of bacteria can significantly improve the efficiency of gene/protein delivery and makes it possible to reduce undesired transfection in other tissues or organs except myocardium. No vectors have exhibited specificity for infarcted myocardium through i.v. injection, and therefore inadvertent transfection of nontarget organs is inevitable[26]. Although various catheter- or surgical-based techniques also have been developed to directly target the myocardium, systemic spread of the vector can occur through the bloodstream or the lymphatic system (washout), most often to the liver or spleen[26]. The present inventors proved that bacteria localized in the infarcted myocardium did not recolonized in other organs such as the liver and spleen evading from the original location (FIG. 1 and FIG. 2). It is very advantageous that gene expression is induced preferentially in targeted tissues. This tissue-specific expression is maximized with remote control of gene expression. Indeed, gene expression using pBAD system of the present invention was turned on by injection of L-arabinose (FIG. 2 and FIG. 3).

Attenuated *S. typhimurium* has been known to have acceptable safe profile[17-29]. Currently, a phase I clinical trial of attenuated *Salmonella* (VNP20009) for 24 patients with metastatic melanoma and one patient with metastatic kidney carcinoma is proceeding, this trial shows that the VNP20009 strain may be injected to patient safly[27]. In a separated pilot experiment using VNP20009 strain expressing cytosine deaminase (TAPET-CD), no side effect was observed after intra tumoral injection of the strain[28].

Although the mechanism of bacterial targeting to infarcted tissues is an intriguing question, it suggested that the infarcted tissue provides protective environment against host immune system for the proliferation of bacteria. Interestingly, the bacterial targeting to infarcted tissues was shown in *S. typhimurium* (ΔppGpp) strain but not in *E. coli* (data not shown). Although wild-type *S. typhimurium* may target to infarcted myocardium, attenuated (ΔppGpp) strain targeted infarcted myocardium more preferentially and proliferated in the infarcted myocardium and this is thought that the attenuated (ΔppGpp) strain induces less immune response (data not shown). The most interesting result is that *S. typhimurium* A1-R strain[7] known to have excellent tumor-targeting ability did not target myocardial infarction. Therefore, solely hypoxic condition can not explain the MI-targeting and proliferation of *Salmonella*. Although the above experimental results focused on the delivery of reporter proteins, it is obvious to a person in the art that angiogenic factors may expressed selectively in the infarcted myocardium based on the experimental results.

In the mean time, given that the bioluminescence reaction requires oxygen, the detection of RLuc8 activity in MI rats suggests that the engineered bacteria were located in the peri-infarct zone, where oxygen is present. Thus, MI targeting bacteria can potentially deliver therapeutic proteins to salvageable myocardium. MI-targeting bacteria opens many new avenues for molecular imaging and therapy, including tissue-specific targeting with signal amplification based on bacterial proliferation, in vivo tissue-specific drug delivery, and the design of imagable therapeutic probes.

II. Selective Targeting to Brain Infarction

Experimental Procedures

Phothochemically Induced Ischemic Stroke Model (Photochemical Infarction)

All experimental procedures were approved by the Chonnam National University Animal Research Committee. Male Sprague-Dawley rats (200-250 g) were anesthesized by i.p. injection of ketamin hydrochloride (50 mg/kg) and xylazine hydrochloride (5 mg/kg) during operating. Body temperature measured by a rectal probe was maintained at 37.0±0.5° C. using a hitting pad. Light was illuminated to cerebral cortex of rats treated with rosebengal and photochemically-initiated thrombosis was induced thereby (Watson B D, Dietrich W D, Busto R, Wachtel M S, Ginsberg M D. Induction of reproducible brain infarction by photochemically initiated thrombosis. (1985) *Ann. Neurol.*, 17: 497-404). Rat's skull fixed on a stereotaxic frame was exposed and a cold white light source (Olympus, Japan) with 6 mm diameter was positioned on the skull at 1 mm anterior to the bregma on right anterial cortex and 3 mm lateral to midline (Paxinos G, Waston C R, Emson P C. AchE-stained horizontal sections of the rat brain in stereotaxic coordinates. (1980) *J. Neurosci. Methods*, 3: 129-149). Rosebengal (20 mg/kg, Sigma, Steinheim, Germany), a photochemical dye was injected into a saphena through a microinjection pump and 2 minute after the injection light was illuminated to the skull for 20 min.

Intercranial Hemorrhage (Bleeding Stroke)

Intercranial hemorrhage (ICH) was induced by the injection of bacterial collagenase into the cranium stereotactically (Jeong et al., (2003) *Stroke*, 34: 225863; Del Bigio M R et al., (1996) *Stroke*, 27: 231220). Particularly, rats were placed on stereotactic frame (Kopf Instruments, Tujunga, Calif.) after i.p. injected with ketamine (30 mg/kg) and xylazine hydrochloride (4 mg/kg). After forming a burrhole, a 30-gage needle was inserted into striatum (0.1 mm posterior, 4.0 mm abdominal, and 2.0 mm lateral to the bregma, respectively) through the burrhole. Then ICH was induced by injecting type IV collagenase (1 saline solution-containing 0.078 U, Sigma) for 5 min. The needle was removed smoothly after 3 min of incubation. During the experiment, body temperature was maintained at 37±0.5° C. by monitoring rectal temperature.

MRI (Magnetic Resonance Imaging)

In order to identify infarcted location, MRI analyses were conducted. The imaging was performed using 3-Tesla, MR scanner (Magnetom Tim Trio, Siemens Medical Solutions, Erlangen, Germany). Rats were anesthesized through a genenal inhalation anesthesia (1.5% isofluran in 1:2 mixted gas of $O_2/N_2$) during imaging. Artificial products according to breathing movement were reduced by fixing rats' heads in a prone position. T2-weighted images (TR/TE=3,000/100 msec, flip angle=150, acquisition time=242) and T2-weighted images (TR/TE=231/10 msec, flip angle=25, acquisition time=256). Other parameters for the imaging are as follows: FOV=7.0 cm, number of matrices=256,192, slice thickness=2 mm, slide gap=0.1 mm and number of excitings=2.0. MRI images were acquired at 2 days after the induction of brain infarction.

Bacterial Injection

Rats were i.v. injected with *S. typhimurium* (ΔppGpp) strain ($5\times10^8$ CFU in PBS), the same strain used in the above experiments for myocardial infarction through tail vein using 1-cc insulin syringes at 2 days after the induction of brain infarction. Wild-type rats were equally operated. In addition, 200 μl of bioluminescent *E. coli* strain ($1\times10^9$ CFU, $1\times10^{10}$ CFU and $5\times10^{10}$ CFU) was injected with the same method. The bioluminescent *E. coli* strain which is a variant strain (MG1655) transduced with an asd gene delivery plasmid comprising a lux operon and asd complement gene was constructed by a known method previously (Silhavy T J et al., (1984) Experiments with gene fusions. New York: Cold Spring Harbor Laboratory Press; Min J J et al., (2008) *Nat. Protoc.*, 3: 629-636).

Optical Imaging Using Cooled CCD Camera System

Experiments were conducted same as the above experiments regarding myocardial infarction using IVIS 100 system (Xenogen-Caliper, Hopkinton, Mass.) equipped with cooled CCD camera. Rats were anesthesized with isofluran before the imaging. Bioluminescence signals within 2 min of exposure emitted from bacteria were detected and imaged.

Histological Analysis and Immunohistochemistry

After imaging, rats were anesthesized with isofluran and perfused with 100 mL of saline solution and 100 mL of 4% paraformaldehyde through the heart. Then rats were decapitated and brains were excised. The brains were fixed with 4% paraformaldehyde for 24 h and kept in a freezer with 30% sucrose solution for 24 h. The freezed brains were sectioned into 10 μm-thick sections using a cryostat. Adjacent consecutive coronal sections were treated for H&E (hematoxylin and eosin) staining. Then, the location of bacteria in the brain was identified using anti-*Salmonella* antibody (1:300, Santa Cruz Biotech, St. Louis, Mo., USA). The brains sections were reacted with the primary anti-*Salmonella* antibody at 4° C. overnight and reacted with Alexa Flour 488-conjugated anti-mouse IgG (1:400, Molecular Probes) at room temperature for 1 h. Nonspecific binding sites were blocked by incubating the sections with PBS containing 10% normal goat serum for 30 min. The tissues were mounted using Slowfade™ Antifade kit (Molecular Probes) and observed with an epifluorescent microscope (Olympus, Japan).

Experimental Results

The present inventors investigated whether *Salmonellae* target brain infarction as well as myocardial infarction. Two brain infarction rat models were used: an ischemic stroke model and a hemorrhage stroke model. For the present, the present inventors produced a photochemically-inducted cerebral ischemic stroke model rats by illuminating light to the cerebral cortex of rats treated with rosebengal. On the next day, the model rats (n=10) were injected with *S. typhimurium* (ΔppGpp) strain ($5\times10^8$ CFU) expressing bacterial luciferase encoded by lux operon. The lux operon encodes all proteins essential for bioluminescence including bacterial luciferase, substrates and substrate-regenerating enzyme. In order to investigate the distribution of *Salmonellae* in the models, whole body images were acquired using cooled CCD camera (IVIS-100, Xenogen-Caliper) (FIG. 16). Bioluminescence signals were detected all over the whole body at 30 min and 1 hour post inoculation and detected in the liver and spleen at 3 hours post inoculation. This result may be due to reticuloendothelial systemic clearance of the organs. However, bioluminescent signals increased significantly in the infarcted brain at 1 dpi and the strongest signals in the infarcted brain were detected at 2 and 3 dpi whereas bioluminescent signals in other internal organs were reduced. Significant level of bioluminescent signal in the infarcted brain was maintained up to 6 dpi. This means that *Salmonellae* can be maintained and proliferate in the infarcted brain for quite a long time. Finally, *Salmonellae* is thought to be eliminated by host immune system. In order to investigate the precise location of *Salmonella*, the present inventors acquired optical images of brains excised from model rats using a cooled CCD camera (FIG. 17). An edematous change which is an indication of brain ischemic infarction was observed (FIG. 17, arrow). Interestingly, the bacterial bioluminescent site was shown to be overlapped with the infarcted hemisphere (FIG. 18, arrow). T2-weighted MR images showed high intensity of image signals, and this represents corresponding brain infarction in the right cerebral hemisphere (FIG. 19, arrow).

Then, the present inventors produced ICH model rats. On the next day, the model rats (n=10) were injected with S. typhimurium (ΔppGpp) strain (5×10$^8$ CFU) expressing bacterial luciferase encoded by lux operon. The lux operon encodes all proteins essential for bioluminescence including bacterial luciferase, substrates and substrate-regenerating enzyme. In order to investigate the distribution of Salmonellae in the models, whole body images were acquired using cooled CCD camera (IVIS-100, Xenogen-Caliper) (FIG. 20). Similar to the ischemic stroke model, bioluminescent signals emitted from Salmonellae were detected all over the whole body early (30 min post inoculation) and then in the internal organs (3 hours and 5 hours post inoculation). However, bioluminescent signals in brain were detected from 1 dpi and the signals increased at 2 and 3 dpi, whereas bioluminescent signals in other internal organs were reduced. The above result shows that Salmonellae target the hemorrhagic injury of rat brain lesion definitely.

In the meantime, the present inventors compared targeting ability of S. typhimurium (ΔppGpp) strain and wild-type S. typhimurium strain directly (n=3, each experimental group). Rats with brain infarction were i.v. injected with S. typhimurium (ΔppGpp) strain expressing lux (5×10$^8$ CFU) and wild-type S. typhimurium strain expressing lux (5×10$^8$ CFU). Intensities of bioluminescent signals emitted from the bacterium at 2 and 3 dpi were compared. Bioluminescent signal of S. typhimurium (ΔppGpp) strain was much higher than that of wild-type S. typhimurium strain (FIG. 22, P<0.01).

Histological analyses for the infarcted brain site of rats having cerebral ischemic infarction of FIG. 7 were carried out (FIG. 21). According to H&E staining, the accumulation of inflammatory cells due to the infiltration of basophiles was shown at the boundary of infarcted site (between the necrotic core and normal brain tissue), which is observed as dark bands (dark arrows in A and C) with (A, B) or without (C, D) the injection of Salmonellae. In higher magnified images (B, D), the level of the infiltration of basophiles was measured with violet staining of cells and the level of liquefaction was high when injected with Salmonellae. Definitely, the case when rats were infected with Salmonellae induced more infiltration of basophiles more than that when there was only infarction without infection of Salmonellae.

Consequently, it is proved that S. typhimurium injected intravenously can colonize selectively at the infarcted brain. This feature of Salmonellae suggests that the bacteria may be used as a drug delivery vector for treating brain infarction.

III. Delivery of Angiogenic Factors to Infarcted Myocardium Using Attenuated Bacteria Plasmids hVEGF165 and hFGF1a were amplified using pBLAST49-hVEGF and pBLAST2-hFGF (Invivogene), respectively. The vectors were diluted to the concentration of 1 µg/µl. Rluc8 gene from pelB-Rluc8 vector was substituted with hVEDG165 or hFGF1a (acidic FGF, isoform 1). The nucleotide sequence and amino acid sequence of VEGF165 are disclosed in SEQ ID NO: 1 and 2, respectively and the nucleotide sequence and amino acid sequence of hFGF1a are disclosed in SEQ ID NO: 3 and 4, respectively. The substituted gene is located downstream of pelB leader sequence. pelB leader sequence consisting of the first 22 codons of pectate lyase B gene of Erwinia carotovora directs the translocation of a protein into bacterial periplasm and then produces a final mature form of the protein by being deleted. Fusion constructs pelB-hVEFG165 or hFGF1a are controlled by an inducible pBAD promoter.

Isolation of hVEGF165 and hFGF1a

PCR primers were designed and synthesized using BioEdit software (Bionics). Sequences of the synthesized primers are as follows:

```
hVEGF165:
                                          (SEQ ID NO: 6)
P1 5'-CATGGCCCAACCGGCCATGGCCATGAACTTTCTGCTGTCTTG
G-3'
(with SfiI site before start codon)

(SEQ ID NO: 7)
P2 5'-AGTGTCGACTCACCGCCTCGGCTTG-3'
(with SalI site and stop codon)

hFGF1a:
                                          (SEQ ID NO: 8)
P1 5'-CATGGCCCAACCGGCCATGGCCATGGCTGAAGGGGAAATC-3'
(with SfiI site before start codon)

(SEQ ID NO: 9)
P2 5'-AGTGTCGACTTAATCAGAAGAGACTGGCAGGG-3'
(with SalI site and stop codon).
```

PCR reactions were carried out using PCR reaction mixtures comprising a vector 1 µl, dNTP 2 µl, i-Taq DNA polymerase (2.5 U/µl) 1 µl, 10×PCR buffer 5 µl, sense and antisense primers 1 µl, respectively and ddH$_2$O 39 µl in the condition of total 40 cycles: 94° C. for 1 min, 56° C. for 1 min, and 72° C. for 30 sec. PCR products were identified using Seakem agarose gel electrophoresis and hVEFG165 (~600 bp) and hFGF1a (~500 bp) fragments were extracted from the gel and purified using Wizard™ SV Gel and PCR Clean-Up system (Promega).

Construction of Bacterial Expression Plasmids, pBAD-pelB-hVEGF165 and pBAD-pelB-hFGF1a In order to ligate hVEGF165 and hFGF1a gene into a target vector, the purified PCR products and pBAD-pelB-Rluc8 vector were cleaved with restriction enzymes (SfiI and SalI). SfiI cleavage was carried out in a reaction mixture of 30 µl comprising DNA 1 µg, the enzyme (2 Unit, BioLabs), 1×NEB4 buffer, 1×BSA and ddH$_2$O at 50° C. for 2 h and the reaction was heat-inactivated at 65° C. for 20 min. Genes to be inserted and a vector fragment (3:1 ratio) were ligated using T4 DNA ligase (NEB) and the resultant recombinant plasmids were transformed into E. coli DH5α.

Transformation of Recombinant pBAD-pelB-hVEGF165 (pBp-hVEFG165) or pBAD-pelB-hFGF1a (pBp-hFGF1a) into DH5α

20 µl of recombinant pBAD-pelB-hVEGF165 or pBAD-pelB-hFGF1a were mixed with 80 µl of competent E. coli DH5α (Invitrogen) and the mixtures were incubated on ice for 10 min. Then, the mixtures were incubated at 42° C. for 45 min and transferred to 900 µl of LB broth in 1.5 ml Effendorf tubes. The mixtures were incubated at 37° C. for 1 h and plated on LB agar plates containing 100 µg/ml of ampicillin and then the plates were incubated at 37° C. overnight. Transformed bacterial clones were cultured in LB broth supplemented with ampicillin.

Transformation of Recombinant pBAD-pelB-hVEGF165 (pBp-hVEFG165) or pBAD-pelB-hFGF1a (pBp-hFGF1a) into Salmonellae (Electroporation)

Recombinant pBAD-pelB-hVEGF165 (pBp-hVEGF165) or pBAD-pelB -hFGF1a (pBp-hFGF1a) were introduced into Salmonella typhimurium (ΔppGpp) strain, SHJ2037 (relA::cat, spoT::kn) by electroporation. The electroporation was performed by applying electrical shock of 1.8 kV for 1 sec and incubating at 37° C. for 1 h. Then, colonies having pBAD-peIB -hVEGF165 (pBp-hVEGF165) or pBAD-peIB-hFGF1a (pBp-hFGF1a) were obtained by plating and culturing transformed bacterial cells on LB agar plates containing 100 µg/ml. In the meantime, for in vivo imaging, pBp-hVEGF165 or pBp-hFGF1a were transformed into attenuated strain having bioluminescent reporter gene lux (Salmonella typhimurium ΔppGpp/lux). In order to investigate whether Salmonella typhimurium (ΔppGpp) strain and Salmonella typhimurium ppGpp/lux were transformed with the vectors, hVEGF165 fragment (~600 pb) and hFGF1a fragment (~500) were identified by obtaining DNA plasmids from bacterial suspensions and treating the plasmids with restriction enzymes (SfiI and SalI). In order to observe bioluminescence of Salmonella typhimurium ppGpp/lux strain, transformed bacterium were cultured on LB agar plates and 1-sec imaging was performed using a CCD camera of an imaging system (IVIS).

Detection of hVEGG165 and hFGF1a Proteins in Bacterial Cells (Western Blotting)

Salmonella typhimurium (ΔppGpp) strain (S.t. ppGpp) and Salmonella typhimurium (ΔppGpp/lux) strain (S.t. ppGpp/lux) were cultured at 37° C. overnight in 10 ml of LB broth/ampicillin media. Bacterial suspensions were inoculated at the ratio of 1:100 in 10 ml of LB/ampicillin and incubated when $OD_{600}$ of the culture reaches to 0.5. Gene expression from pBAD promoter was induced by adding 0.2% L-arabinose to culture media. Bacterium of 2 and 5 hours post induction ($1\times10^7$, $1\times10^8$ CFU, respectively) were pelleted by centrifugation and the pellets were lysed using an extraction reagent (Elpis). The bacterial lysates were applied to an electrophoresis on 12% polyacrylamide gel. Then, proteins were transferred to PVDF membranes and the membranes were reacted with anti-hVEGF165 or anti-hGFF1a primary antibodies (Santa Cruz, 1:1000) at room temperature for 2 h. The membranes were reacted with HRP-conjugated anti-mouse IgG secondary antibody (Santa Cruz, 1:2000) for 2 h and the proteins were detected by ECL detection kit (Santa Cruz).

Effects of hVEGF165 or hFGF1a Expressed from Salmonella (ΔppGpp) Strain on Infarcted Myocardium MI rats (n=10) were i.v. injected with S. typhimurium (ΔppGpp/lux) strain ($2\times10^8$ CFU) and whole body images were acquired using a cooled CCD carmer system (IVS-100). Similar to Salmonellae without a cargo plasmid, bioluminescence was detected in the heart and spleen of MI rats at 1 dpi. Bioluminescence was detected highly in the heart but not in the spleen and liver at 3 dpi. Gene expression was induced by injecting L-arabinose at 3 dpi. Two days after the induction, angiogensis was observed in the infarcted myocardium and this was evaluated with TTC (triphenyltetrazolium chloride) staining.

The above experimental results suggests that S. typhimurium (ΔppGpp) strain may be used for treating infarction by delivering a therapeutic heterologous protein selectively to the infarcted myocardium and expressing the protein therein.

Although specific parts of the present invention was detailed described, it is obvious to a person skilled in the art that these detailed descriptions are merely preferential embodiments and thus the scope of the present invention should not be limited thereto. Therefore, the scope of the present invention should be defined only by to the appended claims and equivalents thereof.

REFERENCES

1. Min, J. J. et al., Nature Protocols 3, 629-636 (2008).
2. Min, J. J. et al., Mol. Imaging. Biol. 10, 54-61 (2008).
3. Yu, Y. A. et al., Nature Biotechnol., 22, 313-320 (2004).
4. Hoffman, R. M. & Zhao, M., Nature Protocols, 1, 2988-2994 (2006).
5. Zhao, M. et al., *Proc. Natl. Acad. Sci. USA,* 102, 755-760 (2005).
6. Zhao, M. et al., *Proc. Natl. Acad. Sci. USA,* 104, 10170-10174 (2007).
7. Zhao, M. et al., *Cancer Res.,* 66, 7647-7652 (2006).
8. Pawelek, J. M. et al., *Lancet Oncol.,* 4, 548-556 (2003).
9. Pawelek, J. M. et al., *Cancer Res.,* 57, 4537-4544 (1997).
10. Dang, L. H. et al., *Cancer Biol. Ther.,* 3, 326-337 (2004).
11. Jain, R. K. & Forbes, N. S., *Proc. Natl. Acad. Sci. USA,* 98, 14748-14750 (2001).
12. Agrawal, N. et al., *Proc. Natl. Acad. Sci. USA,* 101, 15172-15177 (2004).
13. Yazawa, K. et al., *Cancer Gene Ther.,* 7, 269-274 (2000).
14. Yazawa, K. et al., Breast Cancer Res. Treat., 66, 165-170 (2001).
15. Loeffler, M. et al., *Proc. Natl. Acad. Sci. USA,* 104, 12879-12883 (2007).
16. Lemmon, M. J. et al., *Gene Ther.,* 4, 791-796 (1997).
17. Loeffler, M. et al., *J. Natl. Cancer Inst.,* 100, 1113-1116 (2008).
18. Ryan, R. M. et al., *Bioessays,* 28, 84-94 (2006).
19. Brown, J. M. & Wilson, W. R., *Nat. Rev. Cancer,* 4, 437-447 (2004).
20. Brown, J. M. & Giaccia, A. J., *Cancer Res.,* 58, 1408-1416 (1998).
21. Na, H. S. et al., *Vaccine,* 24, 2027-2034 (2006).
22. Loening, A. M. et al., *Nature Methods,* 4, 641-643 (2007).
23. Loening, A. M. et al, *Protein Eng. Des. Sel.,* 19, 391-400 (2006).
24. Lei, S. P. et al, *J. Bacteriol.,* 169, 4379-4383 (1987).
25. Loessner, H. et al, *Cell. Microbiol.,* 9, 1529-1537 (2007).
26. Lyon, A. R. et al, *Heart,* 94, 89-99 (2008).
27. Toso, J. F. et al, *J. Clin. Oncol,* 20, 142-152 (2002).
28. Nemunaitis, J. et al, *Cancer Gene Ther.,* 10, 737-744 (2003).
29. Thamm, D. H. et al, *Clin. Cancer Res.,* 11, 4827-4834 (2005).
30. Song, M. et al, *J. Biol. Chem.,* 279, 34183-34190 (2004).
31. Davis, R. W. et al, Advanced bacterial genetics: a manual for genetic engineering. Cold Spring Harbor Laboratory Press, Cold Spring Harbor, N.Y., USA (1980).
32. Croinin, T. O. & Dorman, C. J., Mol. Microbiol., 66, 237-251 (2007).

SEQUENCE LISTING FREE TEXT

Existing

The invention claimed is:

1. A method of delivering a therapeutic polypeptide or a therapeutic peptide selectively to an infarcted tissue of a subject having infarcted myocardium or infarcted brain, said method comprising intravenous administration of an attenuated strain of *Salmonella typhimurium* deficient in the production of guanosine-3'5'-bisdiphosphate (ppGpp) synthesis, wherein the strain of *Salmonella typhimurium* is engineered to secrete the therapeutic polypeptide or the therapeutic peptide in the infarcted tissue after localization and proliferation therein.

2. The method of claim 1, wherein the infarcted tissue is of the infarcted myocardium.

3. The method of claim 1, wherein the infarcted tissue is of the infarcted brain.

4. The method of claim 1, wherein the therapeutic polypeptide or the therapeutic peptide is selected from the group consisting of vascular endothelial growth factor (VEGF), fibroblast growth factor, placenta growth factor, myogenic protein, angiogenic cytokine, SIKVAV (SEQ ID NO: 5), and neuropeptide Y.

* * * * *